US012589215B2

(12) United States Patent
    Wood et al.

(10) Patent No.:  US 12,589,215 B2
(45) Date of Patent:      Mar. 31, 2026

(54) MECHANICAL RESPIRATOR

(71) Applicant: San Diego State University (SDSU) Foundation, San Diego, CA (US)

(72) Inventors: Kevin N. Wood, San Diego, CA (US); Tyler Lestak, San Diego, CA (US); Jack Lucas, San Diego, CA (US); Ener Arvizu-Munoz, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 797 days.

(21) Appl. No.: 17/995,393

(22) PCT Filed: Apr. 2, 2021

(86) PCT No.: PCT/US2021/025648
    § 371 (c)(1),
    (2) Date: Oct. 3, 2022

(87) PCT Pub. No.: WO2021/203050
    PCT Pub. Date: Oct. 7, 2021

(65) Prior Publication Data
    US 2023/0166070 A1     Jun. 1, 2023

Related U.S. Application Data

(60) Provisional application No. 63/012,632, filed on Apr. 20, 2020, provisional application No. 63/005,151, filed on Apr. 3, 2020.

(51) Int. Cl.
    *A61M 16/12*       (2006.01)
    *A61M 16/00*       (2006.01)
    (Continued)

(52) U.S. Cl.
    CPC ...... *A61M 16/125* (2014.02); *A61M 16/0084* (2014.02); *A61M 16/024* (2017.08);
    (Continued)

(58) Field of Classification Search
    CPC .............. A61M 16/00; A61M 16/0057; A61M 16/0072; A61M 16/0075; A61M 16/0078; A61M 16/0081; A61M 16/0084; A61M 16/024; A61M 16/0816; A61M 16/0875; A61M 16/0883; A61M 16/1005; A61M 16/122; A61M 16/125; A61M 16/20; A61M 16/202; A61M 16/203; A61M 16/204; A61M 16/205; A61M 16/208;
    (Continued)

(56) References Cited

U.S. PATENT DOCUMENTS

| | | | |
|---|---|---|---|
| 5,664,563 A | 9/1997 | Schroeder et al. | |
| 5,931,159 A * | 8/1999 | Suzuki | A61M 16/021 |
| | | | 128/204.23 |

(Continued)

OTHER PUBLICATIONS

International Search Report and Written Opinion received for PCT/US2021/025648, mailed Sep. 1, 2021.

*Primary Examiner* — Joseph D. Boecker
(74) *Attorney, Agent, or Firm* — Gregory P. Einhorn; Arik B. Ranson; Greer, Burns & Crain, Ltd.

(57) ABSTRACT

In alternative embodiments, provided are mechanical ventilators and methods for making and using them.

14 Claims, 26 Drawing Sheets

(51) Int. Cl.
   *A61M 16/10*      (2006.01)
   *A61M 16/20*      (2006.01)

(52) U.S. Cl.
   CPC .......... *A61M 16/20* (2013.01); *A61M 16/202*
   (2014.02); *A61M 16/208* (2013.01); *A61M*
   *16/209* (2014.02); *A61M 2016/0027* (2013.01);
   *A61M 16/0063* (2014.02); *A61M 16/0078*
   (2013.01); *A61M 16/1065* (2014.02); *A61M*
   *16/204* (2014.02); *A61M 16/205* (2014.02);
   *A61M 2202/0208* (2013.01); *A61M 2205/106*
   (2013.01)

(58) Field of Classification Search
   CPC ........ A61M 16/209; A61M 2202/0208; A61M
   2205/106
   See application file for complete search history.

(56)            References Cited

U.S. PATENT DOCUMENTS

| | | | |
|---|---|---|---|
| 6,279,574 | B1 | 8/2001 | Richardson et al. |
| 8,459,262 | B2 | 6/2013 | Ahlmen et al. |
| 10,315,002 | B2 | 6/2019 | Devries et al. |
| 10,350,374 | B2 | 7/2019 | Robinson et al. |
| 10,406,314 | B2 | 9/2019 | Dunkel et al. |
| 10,426,906 | B2 | 10/2019 | Gajic et al. |
| 10,485,945 | B2 | 11/2019 | Stanton et al. |
| 10,561,576 | B2 | 2/2020 | Glenn et al. |
| 10,602,785 | B2 | 3/2020 | Duffy |
| 2007/0125377 | A1* | 6/2007 | Heinonen ........... A61M 16/204 128/204.21 |
| 2010/0252046 | A1* | 10/2010 | Dahlstrom .......... A61M 16/205 128/205.24 |
| 2013/0061852 | A1 | 3/2013 | Heinonen |
| 2016/0287824 | A1 | 10/2016 | Chang |
| 2019/0336713 | A1 | 11/2019 | Piracha et al. |
| 2020/0086075 | A1* | 3/2020 | Mujeeb-U-Rahaman ................... A61M 16/0003 |
| 2020/0368470 | A1* | 11/2020 | Boulanger .......... A61M 16/208 |
| 2023/0122775 | A1* | 4/2023 | Johnson .............. A61M 16/024 128/204.21 |

* cited by examiner

260

THE AFFECT OF CONTINUOUS PEEP ON FLOW RATE

350

350

350

[7] Sealing Surface

357

1 - Inspiratory Port
2 - Patient Port
3 - Expiratory Port
4 - Main Body
5 - Screw Top
6- Sealing Valve

356

[2]

352

[3]

[5]

[6]

[4]

[1]

353

355

354

351

360

MECHANICAL RESPIRATOR

CROSS-REFERENCE TO RELATED APPLICATIONS

This application claims priority to U.S. Provisional Patent Application Ser. No. 63/005,151, filed Apr. 3, 2020, and claims priority to U.S. Provisional Patent Application Ser. No. 63/012,632, filed Apr. 20, 2020, which applications are incorporated by reference herein in their entirety.

FIELD

The present disclosure relates generally to the field of medical devices. Embodiments of the invention relate more particularly to mechanical respirators and ventilators (collectively referred to herein as ventilators) and methods for making and using them.

BACKGROUND

There is a continuous and ongoing need for mechanical ventilators and respirators (ventilators). For example, infectious respiratory diseases can place a significant strain on the supply of ventilators, and health care providers have lacked sufficient supplies of ventilators to properly treat patients in need of them. A current example of this need is due to coronavirus (e.g., COVID-19).

The COVID-19 infection can travel to the lungs and cause a potentially fatal condition called acute respiratory distress syndrome (ARDS). This condition causes the alveoli to fill with fluid, diminishing the lungs' ability to provide vital organs with enough oxygen. ARDS entails severe inflammation of the lungs and can make some portions of the lungs unusable. This causes a dire situation, and many of these patients will need a ventilator to survive.

There is a wide range of estimates for the number of ventilators needed to meet emergency U.S. demand now and in the future, ranging from several hundred thousand to as many as one million. Stockpiles in the government hierarchy range from the federal level to state, and then county governments. In emergencies, the United States usually turns to the Strategic National Stockpile, which is a collection of strategically located warehouses around the country that house critical equipment including ventilators. Recently, due to the rapid spread of COVID-19, hospitals' private supplies were quickly depleted, leading many of them to lean on the Strategic National Stockpile. Unfortunately, the stockpile has shown to be unprepared for the surge in demand. Several hospitals in need around the country have requested access to the reserve, only to be given a fraction of the supplies they asked for or devices no longer in working order.

There is also a drastic disparity in care and equipment in developing nations. Barriers to implementing additional ventilators include but are not limited to high equipment cost, need for education and training, and lack of research in ventilator protocols for resource-poor settings. More advanced nations may have one available ventilator for hundreds of thousands of people, for example, while in other countries no ventilators may be available at all. Even in the United States, only one ventilator may be available for thousands, which is insufficient.

There are several different categories of ventilation devices ranging from emergency resuscitators to portable and transport ventilators, to top-of-the-line ICU-ready ventilators. With COVID-19, for instance, most of the emergency ventilators that have been given EUA designation from the FDA use an Ambu-bag or BVM (bag-valve-mask). An Ambu-bag is most efficient as an emergency resuscitator, but the present inventors have discovered that its application as a ventilator is not ideal.

Some emergency and portable ventilators on the market exist. Examples include the Savell+ and AHP300.

However, there is a need for a low-cost ventilator that is easily accessible, easy to use, and viable for patients. There is also a need for ventilation systems that can be built and maintained on site, for instance using locally sourced and easily accessible components.

SUMMARY

Example mechanical ventilators and respirators (ventilators) can have a robust design and can often be assembled from locally sourced and easily accessible components, avoiding the need for specialized or difficult to source components. Example ventilators can use a solenoid and mixing valve to provide a patient's oxygen-air mixture.

The portability and/or ease of local assembly of example ventilators allows their use in applications that can extend life-saving care to submarines, naval ships, aircraft, field hospitals, and battlefields, among various other environments. Example devices can be made more rugged and mobile than other ventilators and at a fraction of the cost.

Such example devices can be simple to use, shortening necessary training. A cost-effective ventilator as in example embodiment can address existing supply issues by allowing governments and others to increase their stockpile numbers. Robust design and easily available (e.g., locally sourced) components that can be used in example ventilators also can make it easy to maintain and repair, alleviating the need for specialized technicians to travel to hospitals to upkeep.

Example ventilators can be configured for operating in or multiple operating modes, which may be selectable by an operator. For example, COVID-19 patients often need to be put on High Flow Oxygen Therapy (HFOT) when being transitioned on or off a ventilator. An example ventilator system according to example embodiments can include an HFOT setting among other settings to create an all-in-one machine.

According to one aspect of the disclosed embodiments, a mechanical ventilator comprises a fluid flow controller disposed to receive a mixed gas along at least a first line. The mixed gas includes oxygen from an oxygen source and compressed air from a compressed air source/generator operably connected to the fluid flow controller. The fluid flow controller has a fluid flow controller output line operably connected to a patient line, and is controlled by a pneumatic actuator driven by an on-off valve to deliver the mixed gas to a patient line at appropriate intervals where a tidal volume (TV), inspiratory time, and/or peak inspiratory pressure (PIP) arise from fluid forced to the patient as dictated by the fluid flow controller. A controller is provided for controlling the on-off valve.

A second line is disposed to receive the mixed gas, the second line being configured to create a continuous, constantly flowing positive end-expiratory pressure (PEEP) for delivering the mixed gas along a PEEP output line to the patient line. A junction combines the fluid flow controller output line and the PEEP output line, the patient line being operatively connected to and downstream of the junction. A uni-directional valve is disposed within or upstream of the patient line and downstream of the fluid flow controller output line.

According to another aspect of the disclosed embodiments, methods are provided for operating a mechanical ventilator. The mechanical ventilator includes a fluid flow controller disposed to receive a mixed gas along at least a first line, the mixed gas including oxygen from an oxygen source and compressed air from a compressed air source/generator operably connected to the fluid flow controller, the fluid flow controller having a fluid flow controller output line operably connected to a patient line, the fluid flow controller being controlled by an on-off valve to deliver the mixed gas to a patient line at appropriate intervals where a tidal volume (TV), inspiratory time, and/or peak inspiratory pressure (PIP) arise from fluid forced to the patient as dictated by the fluid flow controller, a controller for controlling the on-off valve, a second line disposed to receive the mixed gas, the second line being configured to create a continuous, constantly flowing positive end-expiratory pressure (PEEP) for delivering the mixed gas along a PEEP output line to the patient line, a junction combining the fluid flow controller output line and the PEEP output line, the patient line being operatively connected to and downstream of the junction, and a uni-directional valve disposed within or upstream of the patient line and downstream of the fluid flow controller output line.

An example method comprises: receiving an inspiratory time, patient pressure, and respiratory rate; providing a model that relates the inspiratory time, patient pressure, and respiratory rate to a tidal volume; determining one or more ventilator parameters to achieve delivery of desired breaths to a patient along the patient line using the model; and controlling operation of the mechanical ventilator based on the determined ventilator parameters.

Other features and advantages will be apparent from the following specification taken in conjunction with the following drawings.

DESCRIPTION OF THE DRAWINGS

The drawings set forth herein are illustrative of exemplary embodiments provided herein and are not meant to limit the scope of the invention as encompassed by the claims.

The present disclosure will become more fully understood from the detailed description and the accompanying drawings, wherein.

In the drawings, reference numbers may be reused to identify similar and/or identical elements.

DETAILED DESCRIPTION

Figure 1:
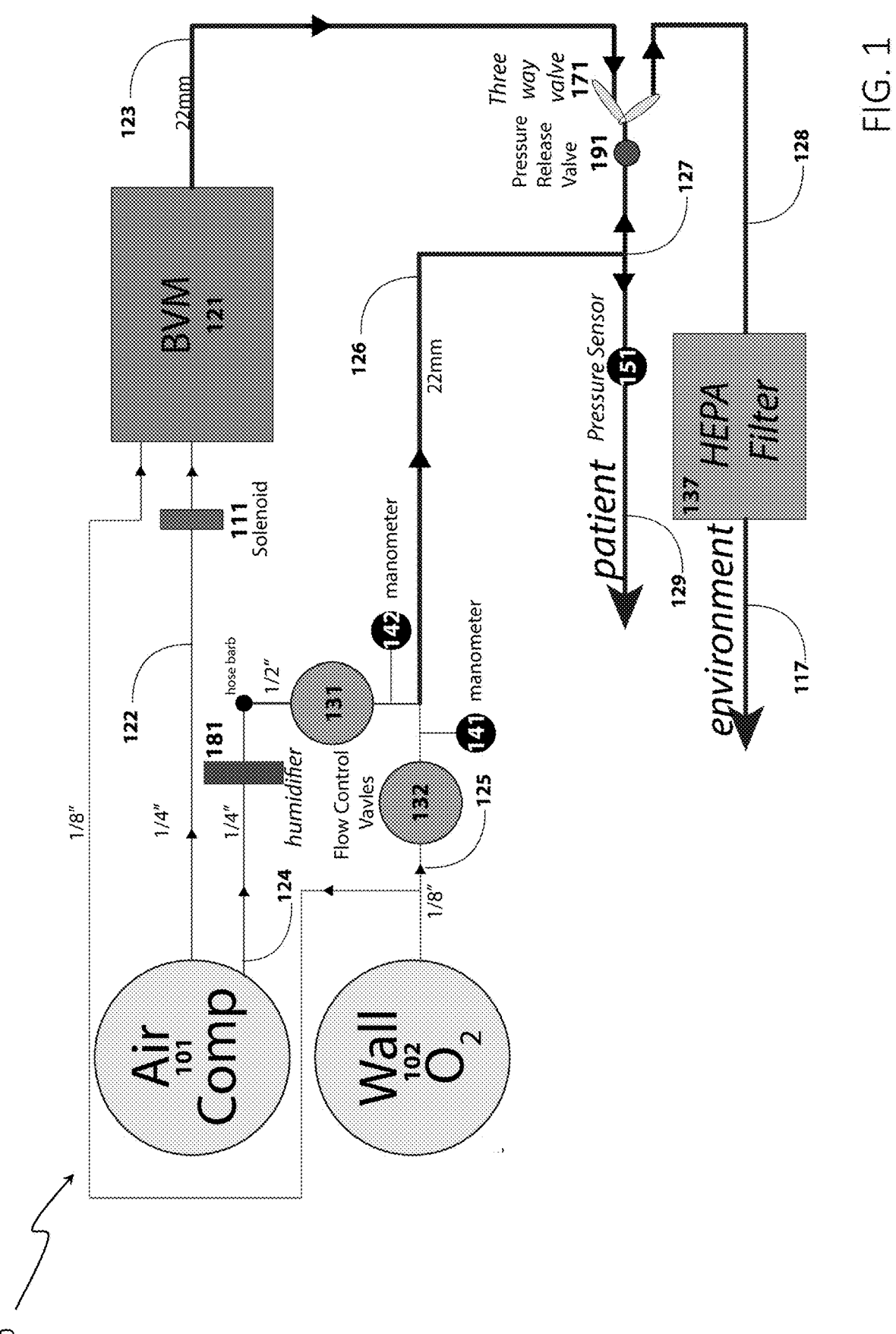
FIG. 1 is a flow diagram illustrating features of a mechanical respirator or ventilator (ventilator) according to a first embodiment.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspects of the invention to the embodiments illustrated.

Example embodiments provide, among other things, a low-cost, easily assembled mechanical ventilation or respiratory system (generally referred to as a ventilator). An example ventilator uses a unique extrinsic positive end-expiratory pressure (PEEP) flow design that can provide a continuous flow of mixed air, e.g., highly oxygenated air, throughout the cycle of ventilation. This flow of highly oxygenated air can reduce $CO_2$ buildup in the lungs, help clear the line of fluid buildup, and increase the tidal volume (TV) ranges.

Example ventilators can be assembled from easily accessible parts, making for simple manufacturing and the potential for local device fabrication. The minimalist nature of some example systems makes them very intuitive and easy to use, though other example systems may include additional features, which may increase complexity. An example device can be made to be simple to operate, requiring minimal training. Moreover, an example rugged design allows for the creation of transport kits that can have a powerful impact on remote areas and in military applications. The unique PEEP flow technology can cater to a wide range of patient needs and minimizes cost.

Example ventilation systems can include a predictive tidal volume (TV) calculation that can utilize a machine-learning algorithm to reduce cost and improve patient safety. In some embodiments, measurements can be displayed on a display such as but not limited to an LCD screen to allow for easy access to vital data. Further, in some embodiments, indicators such as LED indicators and audible and/or visual alarms can be provided that can trigger based on one or more (e.g., from 1 to 12 or more) different conditions to improve safety.

Example ventilators can have several modes of operation, including one or more of Continuous Machine Ventilation (CMV), Intermediate Machine Ventilation (IMV), Spontaneous Continuous Respiration (SCR), and/or High Flow Oxygen Therapy (HFOT), which can be selectable by an operator. Each of these example selectable modes are essential for COVID-19 patients, as one nonlimiting example application. This high level of functionality can rival existing ventilators at a lower assembly cost.

Example ventilators can meet hospitals' growing demands in several markets, including but not limited to nongovernmental organizations (NGOs), developing nations, U.S. Health and Human Services (county, state), and hospital groups.

In alternative embodiments, provided are products of manufacture fabricated, designed or manufactured as mechanical respirators or ventilators, and these respirator or ventilators can comprise a low-cost, easy-to-manufacture, mechanical ventilation system.

In alternative embodiments, mechanical respirators or ventilators or mechanical ventilation systems as provided herein can include one or more of fluid flow controllers, actuators, on-off valves, solenoids, standard tubing, valves, controllers, and common hospital supplies, including but not limited to bags from bag-valve-mask (BVM) assemblies.

In alternative embodiments, mechanical respirator or ventilators or mechanical ventilation systems as provided herein can be upgraded, for example, to be equivalent to and/or to compete with current state-of-the-art mechanical ventilation systems at a fraction of the cost.

In alternative embodiments, mechanical respirator or ventilators or mechanical ventilation systems as provided herein can be portable.

In alternative embodiments, mechanical ventilators or mechanical ventilation systems as provided herein can incorporate one or more manufacturing techniques, or components, or methods of use, or methods for monitoring patients, as described e.g., in U.S. Pat. No. 10,602,785 (describing a filtering face-piece respirator having nose cushioning); U.S. Pat. No. 10,561,576 (describing a negative pressure type respiratory device); U.S. Pat. No. 10,485,945 (describing a patient breathing circuit affiliated with a ventilator); U.S. Pat. No. 10,426,906 (describing a computer-implemented patient information provisioning method); U.S. Pat. No. 10,406,314 (describing an exhalation valve, an inhalation valve, a ventilator and a method for controlling ventilation); U.S. Pat. No. 10,350,374 (describing a medical system having a ventilator coupled to a breathing circuit); and/or U.S. Pat. No. 10,315,002 (describing a ventilator system).

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

Embodiment 1

FIG. 1 shows a ventilation system (ventilator) 50 according to an example embodiment. The example ventilator 50 can be used without exhalation assist. A breath delivery system of the ventilator 50 includes a fluid flow controller embodied in an example embodiment in a bag-valve-mask (BVM) bag 121 and first and second pressure control valves 130, 132. The BVM 121 supplies mixed air, which includes a mixture of compressed air and oxygen. Compressed air for the mixture is provided by a compressed air source/generator such as an air compressor 101 (e.g., wall air, house air, etc.) operatively linked to the BVM, e.g., delivered via an outlet connected to a first line such as a first compressed fluid output line 122. Oxygen is provided by an oxygen source 102 (e.g., wall oxygen, etc.) operatively linked to the BVM, e.g., delivered via an outlet connected to a first oxygen output line. Lines described or shown herein may be provided by one or a combination of hospital grade fluid lines, tubes, conduits, etc., for delivering fluid (including mixed fluid, compressed fluid, etc.) as will be appreciated by those of ordinary skill in the art.

Figure 2:
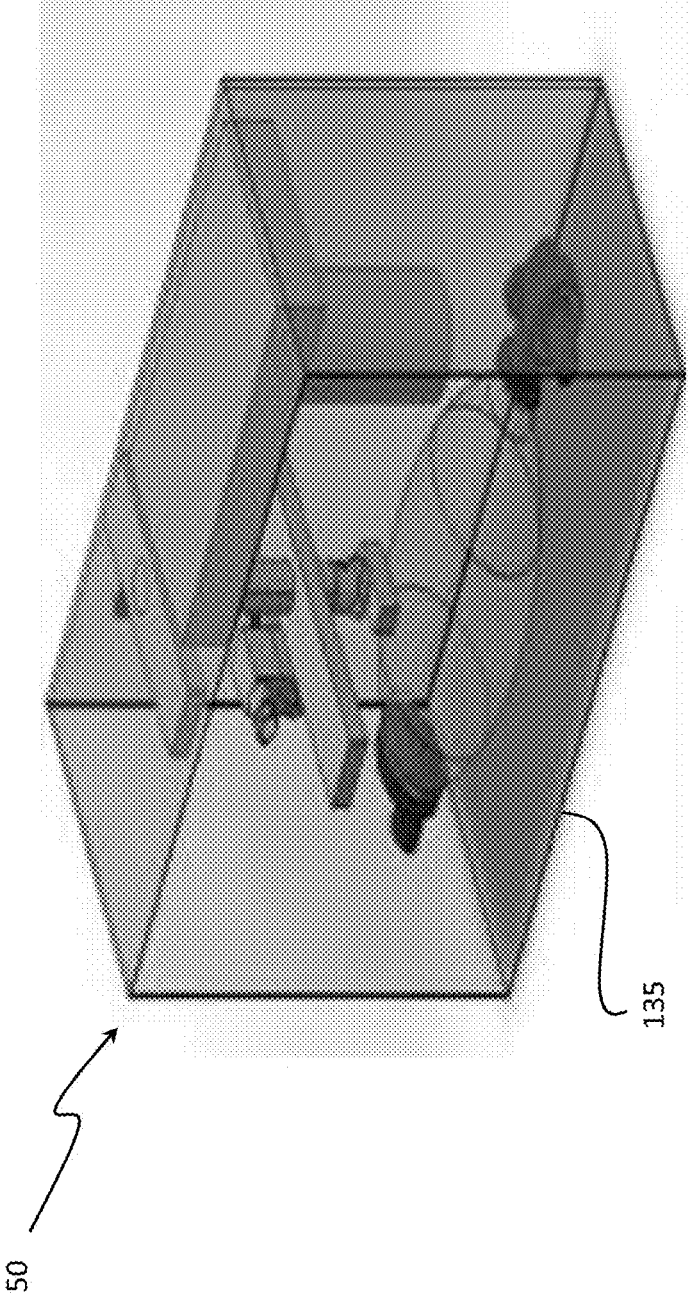
FIGS. 2 and 3 are perspective and elevation views of the mechanical respirator of FIG. 1 in an example housing, which is translucent to show interior features.
Figure 3:
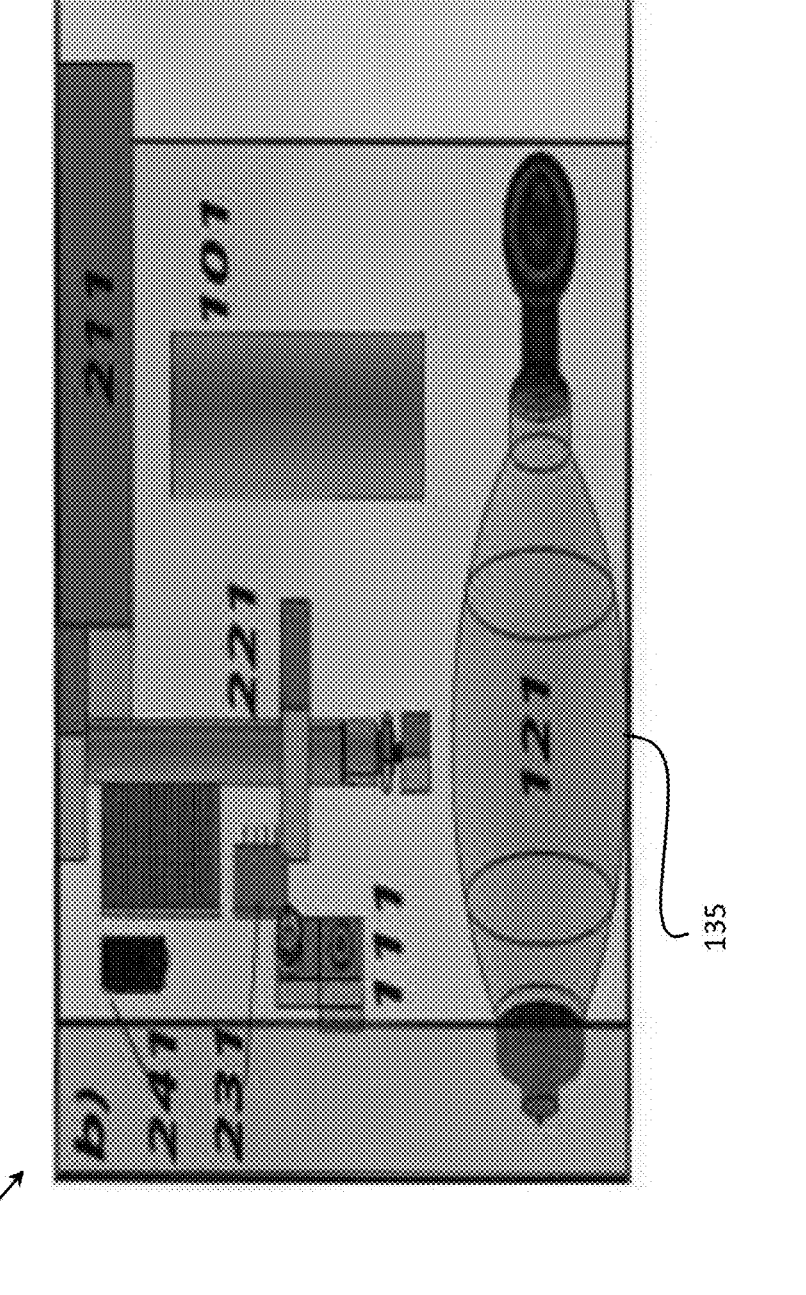

The provided mixed gas from the BVM 121 is delivered from a fluid flow controller output line e.g., a BVM output line 123, in a tidal manner, e.g., at a selectable (e.g., by a controller and/or operator) pressure and volume. The air pressure and volume values can be selectively controlled by an on-off valve. In the example ventilator 50, the on-off valve is embodied in or includes a solenoid 111 that drives an actuator, such as but not limited to a pneumatic actuator 221 (FIGS. 2-3).

The first compressed fluid output line 122 leading from the air compressor 101 delivers compressed air and actuates the pneumatic actuator 221 for the bag-valve-mask (BVM) 121 in the breath delivery system. A nonlimiting solenoid 111 controls the air sent to the pneumatic actuator and is a 24V solenoid valve, which is actuated by a controller and a 24V relay. The relay allows the (e.g., 5V) output of the controller to control the 24V signal used to power the solenoid.

In some embodiments, operation of the fluid flow controller (e.g., BVM) 121 can be triggered, for instance when the patient needs a breath, by a sensor such as a pressure sensor 151 disposed within or in flow communication with a patient line 117 that senses when a patient's breath is attempted. Alternatively or additionally, a patient-operable control, such as but not limited to a push button, switch, etc., can be provided in operable connection with the patient line 117 to allow the patient to manually indicate when a breath is requested. BVM 121 operation can alternatively or additionally be triggered at regularly scheduled intervals that can be determined for each patient using methods known in the art. More than one operation mode may be provided or made available. The solenoid 111, and the pressure sensor 151 can be connected to a suitable controller, e.g., controller 241 (FIG. 3) for operating the BVM 121.

The BVM 121 passes (or moves) the compressed air and oxygen mixture to the patient line 117 via the BVM output line 123, which is in flow communication with the patient line. The tidal volume, inspiratory time, and peak inspiratory pressure (PIP) can be controlled (e.g., dictated) via the compression of the BVM 121.

Oxygen and air ratio in the PIP cycle can be controlled in example embodiments by controlling (e.g., setting, changing, adjusting, maintaining) the oxygen flow rate at the oxygen source 102. The oxygen/air ratio and/or flow rate can be tailored for each patient using methods known in the art.

Additionally, to provide continuous air flow in the example ventilator 50, an outlet from the compressed air source 101 is further connected to a second compressed fluid outlet line 124 arranged and configured to provide continuous positive end-expiratory pressure (PEEP). Similarly, the oxygen source 102 is further connected to a second oxygen output line 125, which is combined (mixed) downstream with the compressed air from the second compressed fluid outlet line 124, e.g., at a junction. In the example ventilator 50, an outlet line from the outlet of the oxygen source 102 is split to provide the first oxygen outlet line leading to the BVM 121 and the second oxygen output line 125 leading to the junction (alternatively, the oxygen source 102 can have multiple outlet lines leading therefrom). A humidifier 181 may be provided in connection with the second compressed fluid outlet line to control humidity of the compressed air.

The continuous air flow can be regulated, e.g., by a valve 130 disposed within the second compressed fluid outlet line 124 and by a regulating valve 132 disposed within the second oxygen outlet line 125. A PEEP flow outlet line 126 downstream from the junction (and thus in communication with the second compressed fluid outlet line 124 and the second oxygen outlet line 125) delivers the combined air and oxygen for PEEP flow.

The continuous air flow, regulated by valves 130 and 132, can create a continuous source of PEEP flow along the PEEP flow outlet line with an ideal (or otherwise configured) oxygen/air ratio to the lungs. This oxygen/air ratio can be determined, for instance, by the respective oxygen and air flow rates, which can be measured in example embodiments using manometers 141 (disposed along the second oxygen output line) and 142 (disposed along the second compressed fluid output line) for measuring and indicating pressure. The manometers 141, 142 can be coupled to a suitable controller, e.g., controller 241, to provide feedback for operating the flow control valves 130, 132.

The PIP flow from the BVM output line of the BVM is combined with the PEEP from the PEEP flow output line at a junction 127 such as but not limited to a T-connection upstream of the patient line 117. Joining together the PIP flow and the PEEP flow allows the patient connected to the patient line 117 to receive breaths while also maintaining enough pressure to keep the lungs open. The PEEP flow improves flow and reduces dead space in the patient line 117.

To scrub the exhalation from the patient, a filter can be placed on the expiratory limb 128. The 3-way check valve 171 forces the exhalation through an air filter such as but not limited to a High Efficiency Particulate Air (HEPA) filter 137 along an expiratory line 128 before reaching the environment through line 117.

Additionally, a safety pressure-release valve 191 may be provided along, e.g., towards the end of, the patient line to regulate pressure to the patient's lungs. The safety pressure-release valve 191 can include or be coupled to a pressure sensor, e.g., coupled to a controller such as controller 241, for monitoring the pressure in the patent line to help ensure safe operating pressures for the patient.

FIGS. 2-3 show the example ventilation system 50, components of which are disposed within a housing 135, e.g., a casing. In example embodiments, all electrical components are coupled to and controlled through a controller embodied in processor 241. Herein, "processor" may include one or several connected processors, and "controller" may include one or several connected controllers. A nonlimiting example processor 241 is an Arduino or equivalent microcontroller (e.g., Arduino Uno, an open-source microcontroller board) with breadboard circuitry. Other example controllers are described herein. The processor 241 can be coupled to a computer and/or display (e.g., an LCD monitor) for additional control, or for analysis and/or display of data.

The PIP flow from the ventilator 50 can be supplied by the compression of the BVM 121 using the pneumatic actuator 221. The pneumatic actuator 221 is powered by compressed air, e.g., from compressed air source 101. In an example operation, the pneumatic actuator 221 is effectively run at about between about 25 psi to about 40 psi, or more generally less than 25 psi. The pneumatic actuator 221 is triggered by the solenoid 111, which can be connected to the processor 241 via a relay 231. The solenoid 111 creates the rhythmic flow of air to the actuator 221.

The processor 241 and solenoid 111 can be operatively connected to a power source 211. One or multiple power sources may be provided in the ventilator 50 for various uses, power demands, and/or environments. For portable, e.g., field use, such as but not limited to non-hospital or makeshift hospital use, for instance, compressed air source 101 can also comprise a battery powered electric compressor which can fit inside of the ventilator housing, as shown in FIGS. 2A-2B.

Embodiment 2

Other embodiments provide mechanical respirators and ventilators and methods for making and using them. In alternative embodiments, provided are mechanical respirators and ventilators including a fully functional ventilator that can perform functions of a conventional ventilator (except for an inspiratory pause), but does not close the expiratory limb of the ventilator system.

In alternative embodiments, mechanical respirators and ventilators as provided herein can have an inspiratory pause that can be used for diagnostic information. Having a system that does not close the expiratory limb is safer and cheaper. In alternative embodiments, mechanical respirators and ventilators as provided herein provide a continuous positive end-expiratory pressure (PEEP) flow.

Figure 4:
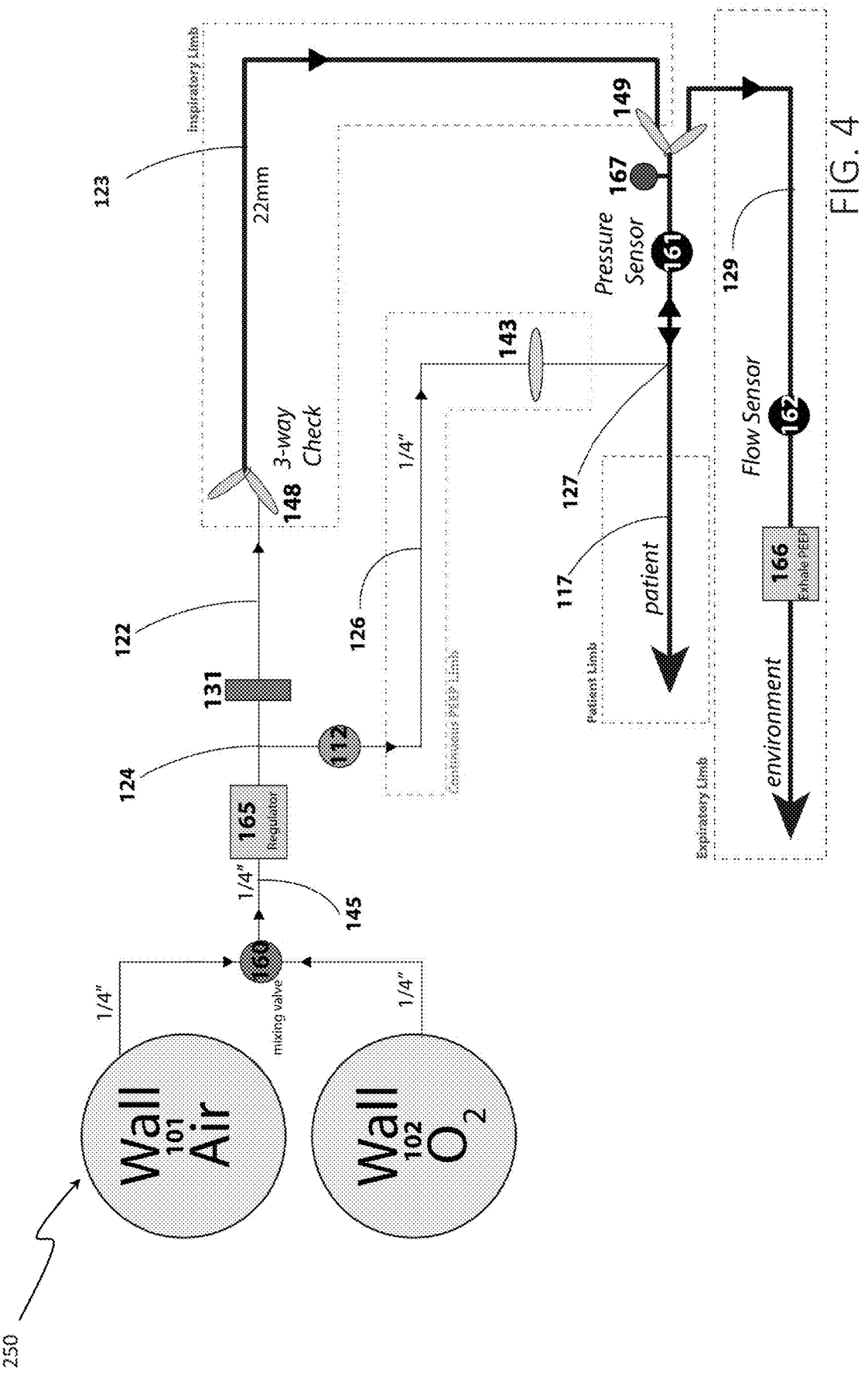
FIG. 4 is a flow diagram illustrating features of a mechanical respirator or ventilator (ventilator) according to a second embodiment.

Referring now to FIG. 4, a ventilation system 250 includes an inspiration cycle triggered by a fluid flow controller that is driven by an on-off valve. The example on-off valve in the ventilation system 250 is embodied in or includes a solenoid valve 131 that directly controls a compressed fluid. The on-off valve, e.g., the solenoid valve 131, is disposed upstream of an inspiratory limb that in turn is disposed between a regulator 165 and a uni-directional valve. In the example ventilation system 250, the uni-directional valve is embodied in a three-way check valve 149. A non-limiting example solenoid valve 131 is a solenoid having a low $C_v$ (Flow coefficient) solenoid valve.

In an example air delivery operation, the solenoid valve 131 is used to directly control the flow of compressed fluid to the patient line 117, via the fluid flow controller output line 123. An example solenoid valve 131 utilizes coiled wire and a metallic plunger to open and close an orifice quickly. When the solenoid valve 131 is powered, current flows through the solenoid, creating a magnetic field that lifts the plunger, allowing the air to flow through the valve. When the current is stopped, a spring pushes the plunger down, closing the valve. In an example ventilator 250, the microcontroller 241 can send pulses to open or close the solenoid. The time that the valve 131 is held open or close can be determined, for instance, by user inputs for inspiration time and respiration rate.

The example solenoid valve 131 allows fast and accurate actuation timing of the valve, as opposed to designs that utilize linear actuators and rotating cams to compress a BVM. BVM-based ventilator designs use an electronic or pneumatic actuator to compress the BVM to pump more air, which may be less efficient, and more complex processing may be performed to translate the linear or rotational movement into a value of expelled tidal volume. The example solenoid valve 131 may also be less expensive and require less manufacturing than mechanical accessories necessary to compress the BVM.

Upstream of the inspiratory limb, the compressed air source/generator 101 (for example, wall air or house air) and the oxygen source 102 (for example, wall oxygen, or another oxygen source which may be concentrated from the air) are delivered via compressed fluid (e.g., air) and oxygen output lines to a mixing valve 160, where gases are mixed, and flow is controlled. The air and oxygen delivered to the patient are controlled by the mixing valve 160. In example embodiments, the mixing valve 160 can control the mixing from 21% to 100% oxygen.

The mixing valve 160 leads to a mixed gas output line 145 for providing a mixed gas (e.g., mixed compressed air and oxygen gas) to the ventilator 250. Fluid such as air can come from an external compressed air reservoir, or be created as part of the example system 250 through a series of fans and pumps. Oxygen can come from a compressed oxygen source 101 or be created by an interconnected oxygen concentrator. Alternatively, a mixed gas input can be provided in the ventilation system 250 by other sources and connected to the ventilator 250, e.g., via the mixed gas input line 145. For instance, a gas mixer can be used by a hospital if desired.

Downstream of the mixing valve 160 or other mixed gas input, the mixed gas (i.e., mixed compressed air and oxygen gas) is delivered via the mixed gas output line 145 to a regulator 165, which controls gas pressure. A splitter that is operatively connected to the mixed gas output line splits the mixed gas output line into first line (e.g., a first compressed fluid output line) 122 and second line (e.g., a second compressed fluid output line) 124.

The mixed gas then passes through the solenoid valve 131 (an example on/off valve) disposed along first line 122 entering the inspiratory limb. In this way, all or only part of the mixed oxygen/air fluid to be delivered to the patient passes through the on/off valve. As used herein, ordinal terms such as "first", "second," etc. are not intended to imply or require any particular order, but are used for convenience. The flow in the line 122 leaving solenoid valve 131 can affect tidal volume (TV) and peak inspiratory pressure (PIP). Additionally, the flow in line 126 affects both tidal volume (TV) and peak inspiratory pressure (PIP), and thus the pressure can be controlled in example embodiments by the throttle valve 112 to control TV.

The regulator 165 can be controlled by a controller, such as provided by a suitable processor. The controller, for instance, can be embodied in system electronics, which can be controlled remotely or automatically, for example, by a computer, or by a health care worker to deliver the same TV at various inspiration times. An additional uni-directional valve located on line 126 can help to help prevent back pressure in the ventilator 250. A 3-way check valve 148, can be provided as an additional safety feature within the inspiratory limb (e.g., within the line 122) to allow the patient to take an emergency breath in the event of solenoid 131 failure. A fluid flow controller outlet line 123 leading from the valve 148 is operatively connected to the three-way check valve 149, which is described in more detail below.

Figure 11:
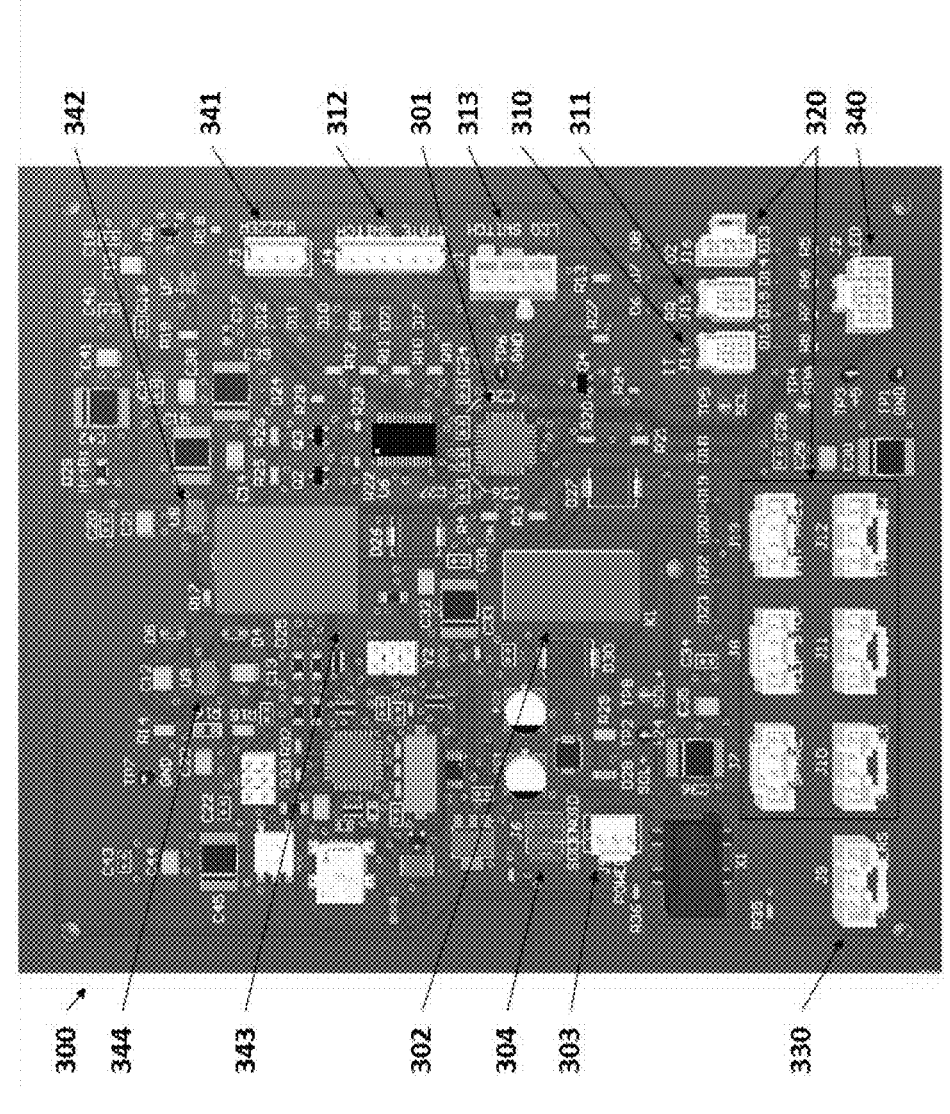
FIG. 11 illustrates an example Printed Circuit Board Assembly (PCBA) incorporating an example controller.

In an example embodiment, the on/off valve, e.g., the solenoid valve 131, is controlled by a processor, such as a microcontroller 241, and a relay 231, as shown in FIGS. 2-3. In some example embodiments, the microcontroller 241 and relay 231 are incorporated into a Printed Circuit Board Assembly (PCBA) 300, an example of which is shown in FIG. 11 and described in more detail below. The processor 241, alone or in combination with additional processors, may be used for controlling all electrical components of the ventilator 250. The controller 241 and solenoid valve 131 can be connected to the power source 211.

For portable use, e.g., field (for example, non-hospital or makeshift hospital) use, the compressed air source 101 can also be a battery powered electric compressor, which in an example embodiment can fit inside of a housing such as a ventilator housing 260 shown in FIGS. 7-10. Other components of the ventilator 250 can also be disposed within the housing 260.

For the mechanical ventilation system, the inspiration cycle is triggered by the solenoid valve 131. In an example operation, the solenoid valve 131 creates the rhythmic flow of gas to the patient, controlling both inspiration time and breath rate. If desired, the solenoid valve 131 can be triggered by a pressure sensor 161 in the patient line 117 that is configured and provided for use by a patient. The pressure sensor 161 can be in communication with the solenoid valve 131 (e.g., both may be connected to the controller 241) to actuate when the patient needs a breath (e.g., trigger inspiration on patient breaths) and/or at regularly scheduled intervals as deemed necessary for each patient.

In example embodiments, the mixed gas output line 145 (after leaving the mixing valve 160) splits downstream of the regulator 165 and upstream of the solenoid 131 via the splitter. The first compressed fluid line (first line) 122 from this split leads to the inspiratory limb via solenoid valve 131. A pressure sensor 163 can be provided at or near this split to provide an accurate reading of the overall system pressure.

A second compressed fluid line (second line) 124 from the split includes a valve 112, e.g., a throttle valve, that leads to a continuous positive end-expiratory pressure (PEEP) limb including PEEP line 126. The PEEP limb controls the mixture of a PEEP flow going to the patient via the patient line 117. For instance, after passing through throttle valve 112, a continuous PEEP line 126 passes through a check valve 143, and then to a patient limb that includes the patient line 117. From this split, the throttle valve 112 can control the flow/pressure of the continuous PEEP limb going to the patient. A pressure sensor 164 may be provided within the continuous PEEP line 126 to measure the pressure of the PEEP flow line. The patient line 117 can further include a pressure-release valve 151 and the pressure sensor 161, which are upstream of the output to the patient.

In an example embodiment, the continuous PEEP line 126 arrives to a junction 127 with mixed air from the fluid flow controller output line 123 just before the patient line 117 to help reduce $CO_2$ build-up. The junction 127 can be any suitable junction for combining fluid lines. During expiration any additional flow can exhaust out an expiratory limb including expiratory line 129. The expiratory limb includes the expiratory line 129, which can lead to the environment. An exhale PEEP regulator 166 in the expiratory line 129 provides an adjustable PEEP value to ensure a specific pressure remains in the patient's lungs after exhale. A flow sensor 162 can be provided in the expiratory line 129 to measure flow through the expiratory limb. This value can be used, for instance, to calculate the tidal volume (TV) per breath.

The expiratory line 129 and the patient line 117 are connected to and downstream of uni-directional valve 149, which is further connected to the inspiratory limb (and continuous PEEP line 126) via fluid flow controller output line 123. In some example embodiments, to help reduce $CO_2$ build-up, the continuous PEEP limb connects to the inspiratory limb at the junction 127 as closely to the output (i.e., to the patient's lungs) as possible, and/or in some examples within an intubation tube. Valve 149 is embodied in a 3-way check valve, which is configured to operate to close the expiratory limb of the system when an inspiratory pulse is delivered, but also to close the inspiratory limb during exhalation to prevent backflow and maintain PEEP. In the example ventilator 250, the continuous PEEP output line 126 is connected to the patient line 117 and to the mixed gas from the fluid flow controller output line 123 at the junction 127, which is disposed downstream of the valve 149 (that is, the junction 127 can be disposed on the patient side of the valve 149).

During inspiration, the PEEP flow helps to increase tidal volume (TV) not otherwise attainable by the low $C_v$ (Flow coefficient) solenoid valve 131 in example embodiments. Low $C_v$ valves are prevalent on low-cost solenoids, for instance. On the patient limb near valve 149, a relief (pressure-release) valve 167 can be provided to regulate the pressure to the patient's lungs, e.g., to ensure a patient's lungs never receive unsafe pressure.

The pressure sensor 161, flow sensor 162, pressure sensor 163, and pressure sensor 164 can be operatively connected to the controller 241. In example embodiments, all data (pressure and flow) from the sensors 161 (pressure), 162 (flow), 163 (pressure), and 164 (pressure) can be visualized through a connected LCD screen or similar display or monitor that is connected to the controller 241.

In example mechanical ventilators, positive end-expiratory pressure (PEEP) is used to maintain sufficient pressure in a patient's lungs to keep them open, while breaths are delivered in addition to the PEEP. PEEP is normally generated through a pressure (e.g., back-pressure) regulator that prevents the patient from being able to expire air at pressures lower than the desired setting. While this helps keep the patient's lungs open, it can leave $CO_2$ in the patient's lungs, causing a drop in peripheral capillary oxygen saturation ($SPO_2$) levels. This can be a critical problem, for instance, with ventilating COVID-19 patients.

To help address this issue, exemplary ventilators 50, 250 as provided herein can also supply a continuous mixture of oxygen and air through the continuous PEEP limb to the patient limb, thereby reducing $CO_2$ build-up in the patient's lungs and improving $SPO_2$ levels. This can also help reduce overall system component costs. This continuous mixed gas supply, referred to herein as continuous PEEP, can be provided, for instance, by the BVM 121 shown in FIG. 1 and by the continuous PEEP limb shown in FIG. 4.

Moreover, example ventilators 50, 250 are also capable of supporting low-tidal volume (TV) therapy. As suggested by some studies, this can be an effective means of treating patients such as COVID-19 patients.

Another specific concern of COVID-19 patients is frequent coughing. An inspiratory pulse occurring at the same time as a cough could be extremely dangerous to a patient's lungs. To mitigate this risk, the relief valve 167 in the patient limb can be configured and operated to exhaust at a selected pressure, e.g., as set by the controller 241 and/or an operator such as a medical provider. Moreover, if interval breathing is being used, relief valve 167 in combination with valves 148 and 149 allows a patient to get a spontaneous emergency breath (of room air) at any moment (e.g., even when Continuous Machine Ventilation (CMV) mode is selected, as described in more detail below), and prevent dangerously unsafe pressures from being delivered after the spontaneous breath. This scenario conventionally has required expensive and sophisticated electronics to be handled safely, but in example embodiments herein this can be handled mechanically by the combined function of valves 167, 148, and 149. The example valves 148, 149, 167 can offer precise control of the system, and do not require a two-solenoid system to control the inhale and exhale functions.

Operators such as respiratory therapists typically control inspiration time, tidal volume (and in some cases inspiratory pressure), and inhale: exhale (I:E) ratio. Each of these variables can be controlled by controlling one or more parameters on example ventilators. In some example embodiments of the system, manual control of parameters can be utilized, reducing component cost. As a non-limiting example, one or more of the valves may be hand-turnable to adjust or tune them as needed. For instance, one or more potentiometers, e.g., knobs, may be provided to allow the operator to adjust the inspiration time and respiration rate as well as a mixing valve to allow the user to control the oxygen to air ratio.

In other example embodiments, control of one or more of the above can be performed at least in part remotely and/or automatically, e.g., by an algorithm. An example control algorithm can be incorporated into the logic of the controller 241, handled by software for a computer connected to the controller 241 for controlling the system, or a combination of these. A combination of manual control and automatic (e.g., algorithmic) control can also be provided. Manual control can be configured to override automatic control, or vice versa, if desired.

An example control algorithm can include one or more models that process input ventilator parameters (control inputs) and sensor inputs (e.g., data for pressure and flow inputs from one or more of sensors 161, 162, 162, 164) to control the ventilator 250, and controlling one or more of the mixing valve 160, regulators 165, 166, solenoid 131, valves 148, 149, 143, and relief valve 167. In example embodiments, the data collected from the sensors 161, 162, 163, 164 is provided as inputs to the control algorithm to create a predictive tidal volume (TV) metric. Example operating methods using such methods can help reduce cost of the ventilator while also giving operators a high degree of information about the system operation and patient health.

Figure 5:
FIG. 5 illustrates graphics demonstrating a high degree of correlation between input parameters and health care metrics of ventilation.
Figure 5:
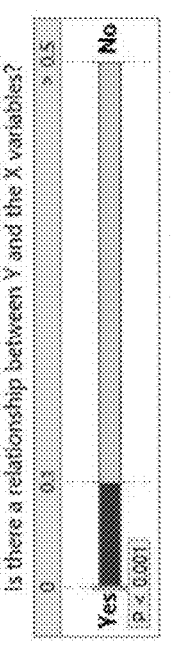
Figure 5:
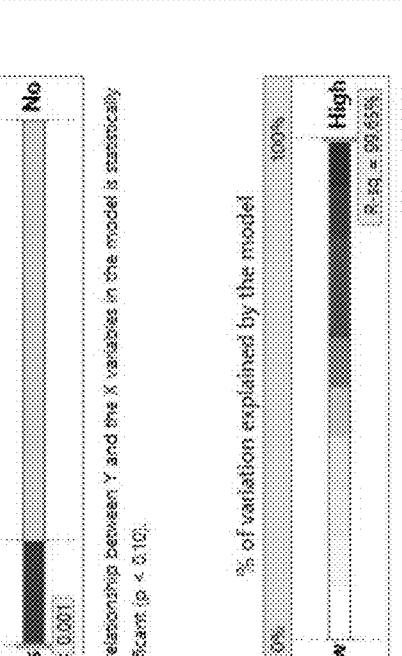
Figure 5:
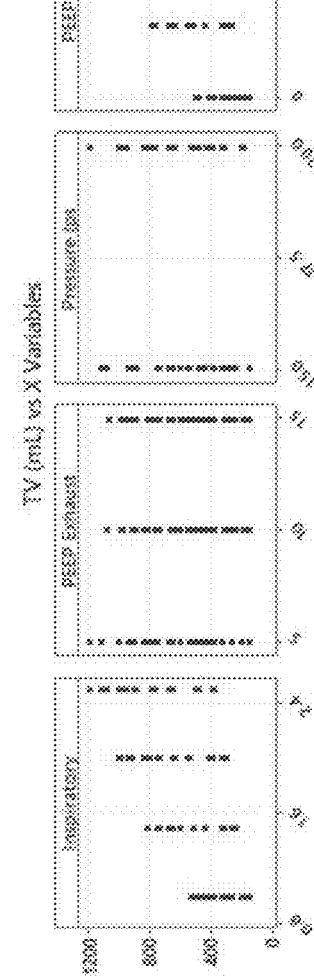
Figure 6:
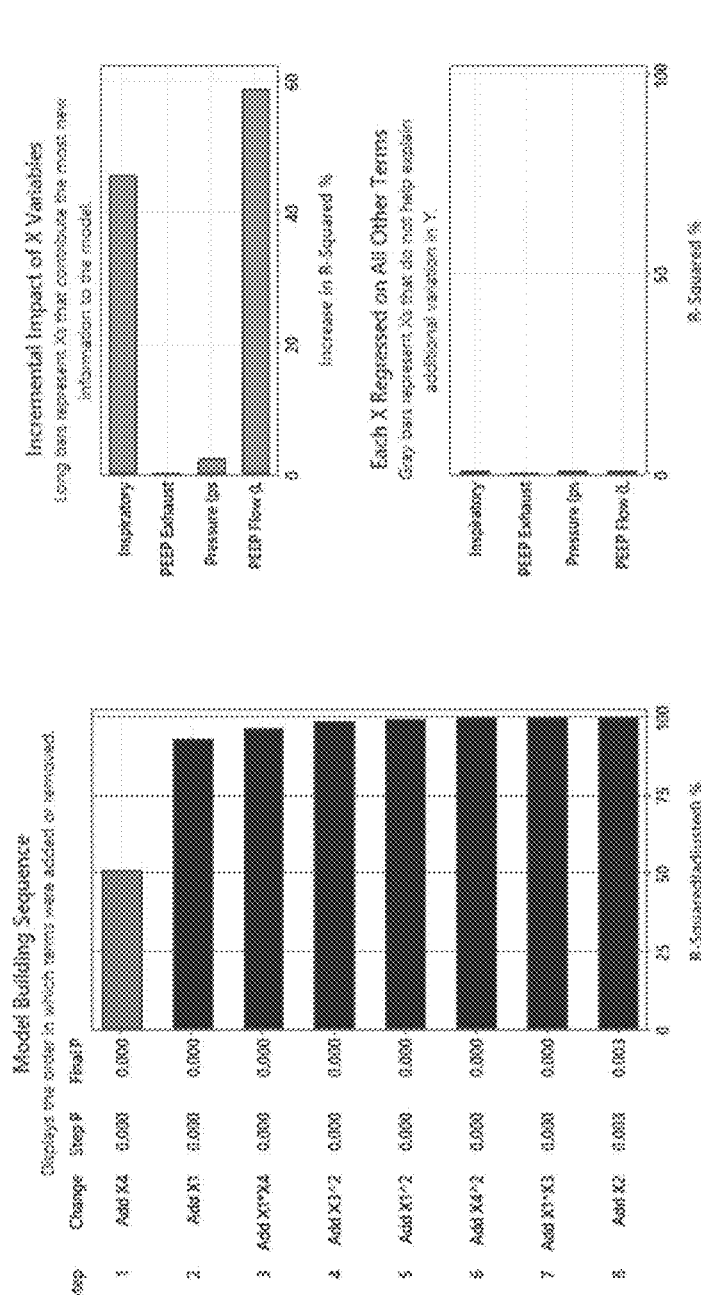
FIG. 6 illustrates and exemplary model relating ventilator parameters to health care metrics of interest.
Figure 7:
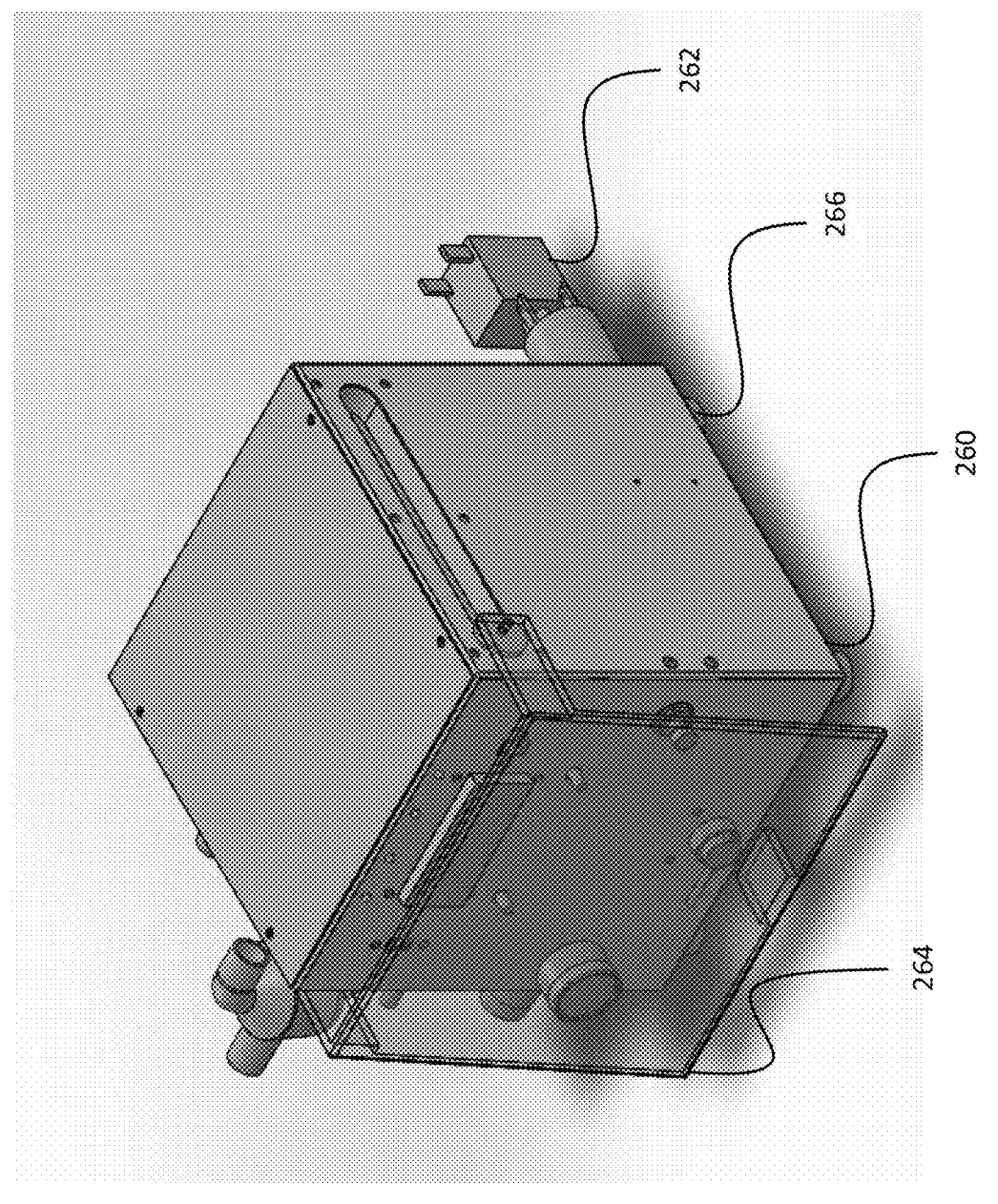
FIG. 7 is a perspective view of an example housing for the mechanical respirator of FIG. 4.
Figure 8:
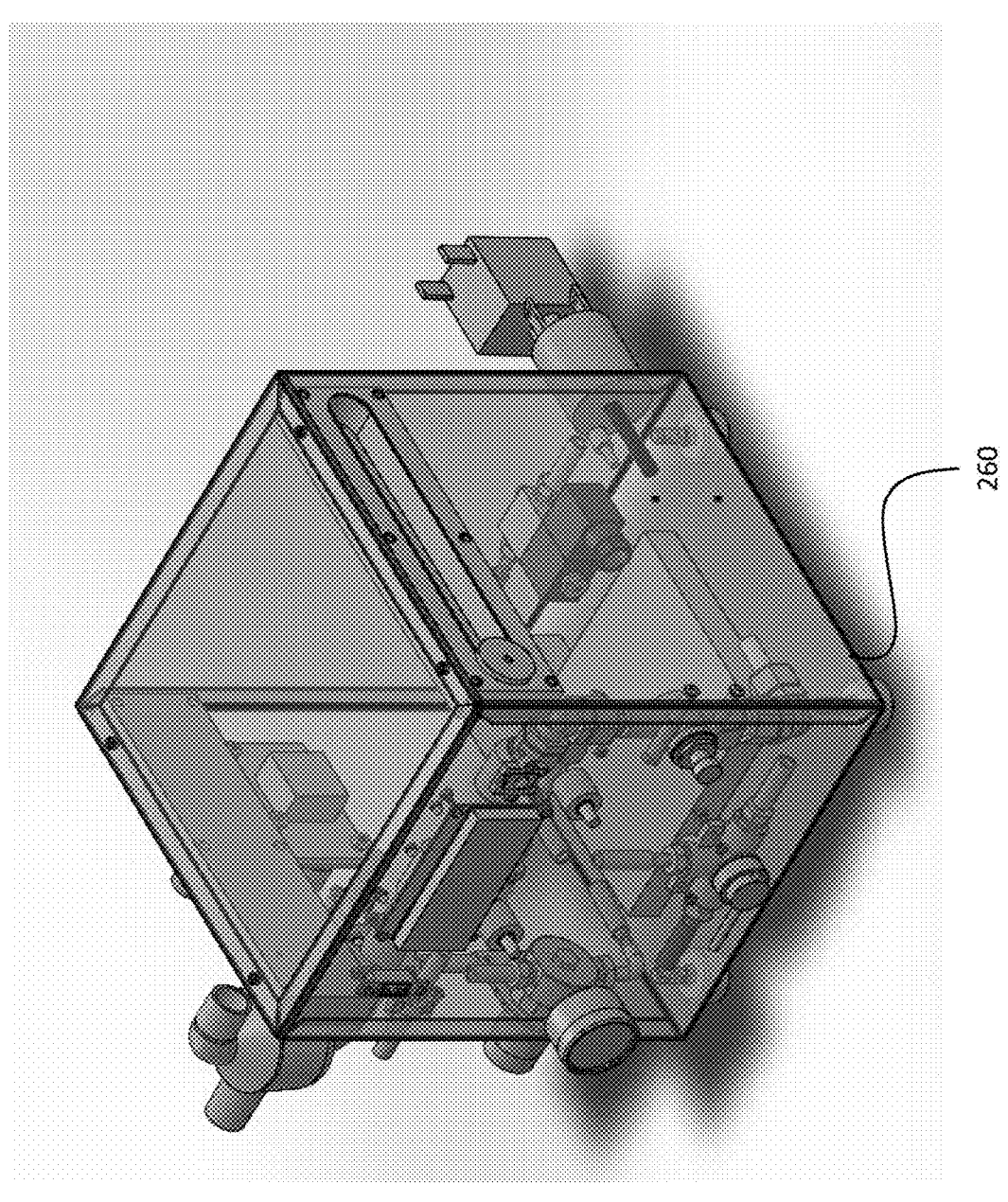
FIG. 8 is a perspective view of an example housing for the mechanical respirator of FIG. 4, showing interior features.
Figure 9:
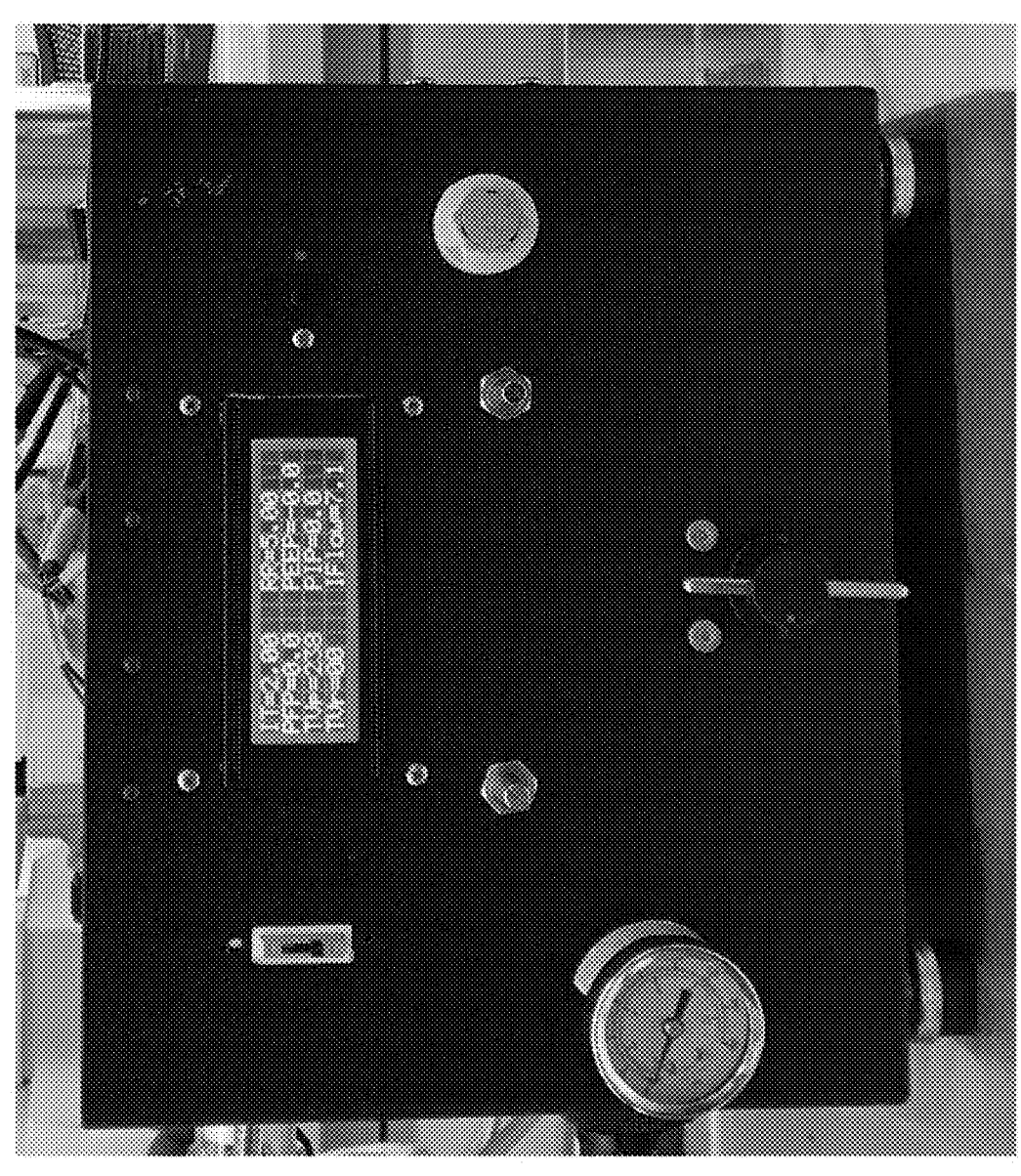
FIG. 9 shows a portion of the housing of FIGS. 7-8, including an activated LCD monitor.
Figure 10:
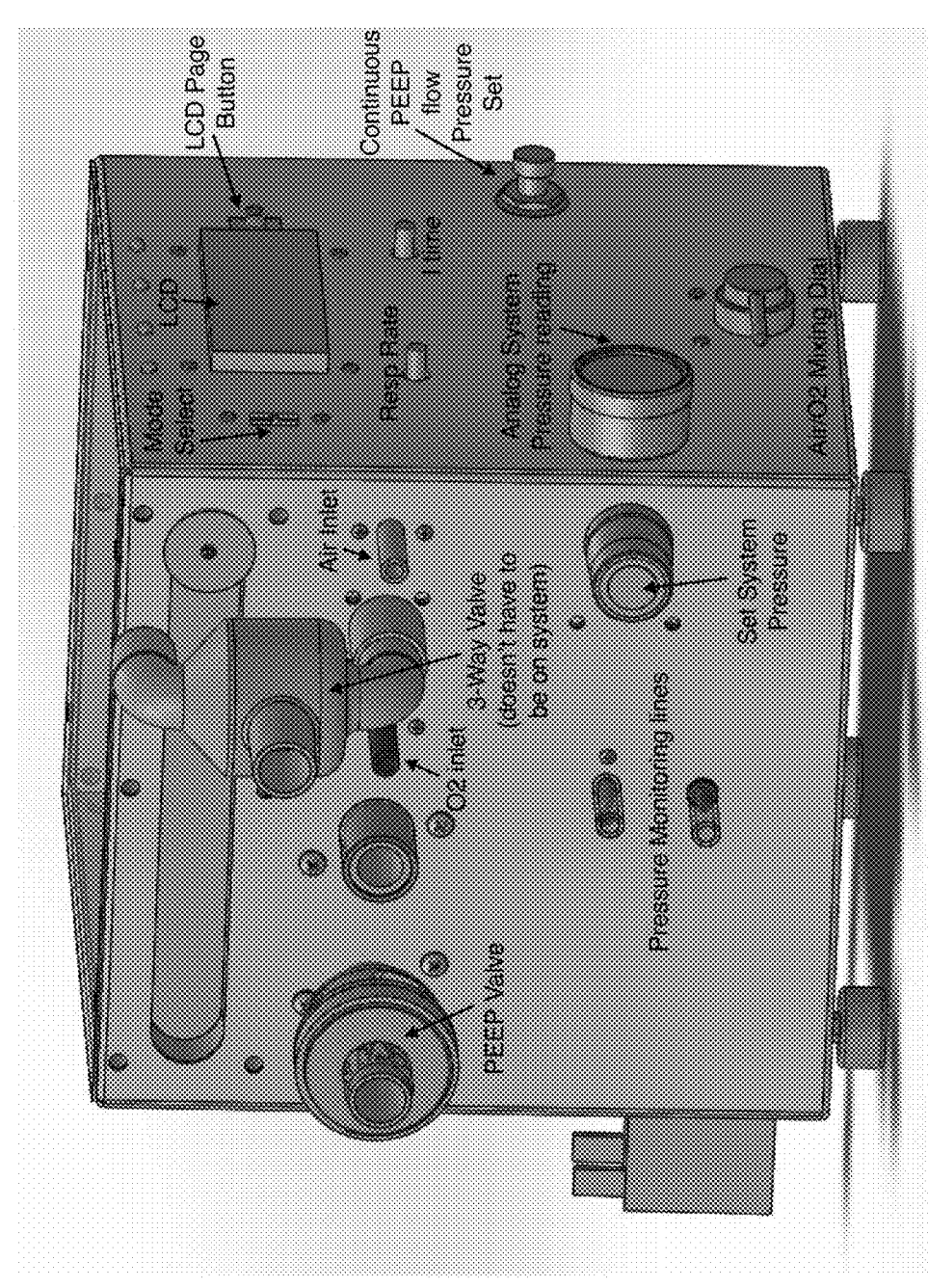
FIG. 10 illustrates a portion of the housing of FIGS. 7-8, showing external features.

FIG. 5 and FIG. 6 demonstrate an example relationship between ventilator control inputs (including inspiratory time (e.g., in seconds), PEEP exhaust (e.g., cmH2O), system pressure (e.g., psi), and PEEP flow (e.g., L/min) and patient variables such as tidal volume (TV). FIG. 5 shows an example regression analysis relating the above parameters and variables. Good model fitting allows the example regression model to be used to predict TV (a Y value) for specific values of the control inputs (X values), or alternatively to determine settings for control inputs corresponding to a desired value or range of values for TV. FIG. 6 shows an example regression model that can be used, e.g., directly, by operators (e.g., health care workers) to define ventilator parameters that can be employed to achieve the desired breaths delivered to the patient. Alternatively, this model, alone or in possible combination with a machine learning algorithm, could be used by the processor 241 and/or computer to predict system performance and patient health. The machine learning algorithm, for instance, can be trained (or iterated) to improve the regression analysis.

Sensor inputs from one or more sensors 161, 162, 162, 164 can be used for feedback to control the ventilator according to the input parameters. For instance, the measured value from the pressure sensor 164 along the PEEP flow line can be used to more accurately calculate the expected tidal volume and give a real time update on that value.

In example embodiments, the ventilator 50, 250 can provide one or more of the following:

Deliver a desired respiratory rate between 10-40 breaths per minute,

Provide a tunable extrinsic positive end-expiratory pressure (PEEP) up to about 20 cm $H_2O$, Provide a tunable maximum peak inspiratory pressure (PIP) limit between 40-100 cm $H_2O$, Supply a tidal volume (TV) of up to 1100 mL in a minimum of about 0.4 seconds (up to about 240 L/min) with a peak inspiratory pressure (PIP) of no more than 40 cm $H_2O$, Control the humidity and/or oxygen mixture of the gas supply, Trigger inspiration on patient breaths, Scrub expired air through a HEPA or equivalent filter, and/or Adjust a mixture (e.g., $O_2$ and air) of the supplied mixed air.

Example ventilators can be provided at low cost and can be assembled by a person with little knowledge of respirators or ventilators.

In operation, an operator (e.g., a health care worker) can apply the ventilator to an individual in need (e.g., a patient). As described above, ventilators can be operated manually, remotely, automatically, or in any combination of these.

Some example ventilators can be controlled manually and/or via the controller 241 or a coupled computer to operate in one or more respiratory modes. Respiratory modes can be selectable by the controller 241, by an operator, or in combination. Four example respiratory modes, ranging from full operator control to full patient control (with assistance as needed or desired from the controller 241) include:

CMV—Continuous Machine Ventilation: The ventilator only delivers breaths as set by an operator, e.g., a health care worker. This mode delivers breaths at a set respiration rate, which is determined by the healthcare professional. This mode will deliver breaths regardless of the patient's breathing cycle.

IMV—Intermediate Machine Ventilation: This mode will deliver breaths at a set respiration rate but will also allow the patient to trigger their own breath. Upon the patient attempting a breath, the machine will deliver a set tidal volume, and reset the breath cycle timer. If the patient does not trigger a breath within the time of the set respiration rate, the machine will deliver one. The volume and/or duration of breath can be set by an operator.

CSR—Continuous Spontaneous Respiration: only the patient determines when the breaths are taken. This mode does not have any timed machine breaths. The patient trigger is the only way a breath will be delivered. However, if the patient does not trigger a breath within the minimum breath per minute count, an alarm will sound.

HFOT—High Flow Oxygen Therapy: This mode delivers a constant, low pressure flow of high-concentration oxygenated air to the patient. HFOT is specifically used, for instance, in COVID-19 patients as an alternative to full ventilation. This process can provide the patients with adequate PEEP to prevent the collapsing of lungs while also providing enough oxygen to keep SpO2 levels high.

The above modes may be selectable, for instance, by providing a switch such as a 4-way switch connected to the controller that that allows the user to select the breathing mode between IMV, CMV, CSR, and HFOT. If fewer modes are used, a 3-way or 2-way switch may be provided.

Feedback can be provided to the operator via the computer, e.g., using a connected display. This feedback allows the operator to monitor the ventilator settings and/or outputs. In some example embodiments, a monitor embodied in an LCD screen is provided with two toggled screens that show all necessary data for each respiration cycle. Alternatively, or additionally, indicators, such as LED and sound alarms, may be connected to the controller 241 and/or computer and provided for alarm conditions such as but not limited to low and high pressure, low flow and high flow, circuit disconnection, or low oxygen ($FiO_2$), which may be detected using suitable sensors and monitoring algorithms.

In some example embodiments, the computer can be configured via suitable software or firmware to include a function that calculates an expected tidal volume and compares it to the measured tidal volume. This feature ensures that the example system is delivering the proper tidal volume (TV) to the patient for the current settings and will alert the healthcare worker if there is a large error in this value.

Example embodiment ventilators 50, 250 can include an easily understandable interface and simple controls to allow the ventilator to be easily used in times of emergency when training is obsolete. As non-limiting examples, an example interface can include visual interfaces (graphs, charts, images, etc.) indicating one or more of minute volume, breaths per minute, I:E ratio, compliance, maximum flow, or system pressure. One or more alarm codes may be provided for display alert the user to any current issues on the system.

FIGS. 7-10 show the example ventilator 250 including components that are contained in and/or on a housing 260. The example housing 260, which may be made of any suitably durable material, e.g., aluminum or stainless steel, is sized and shaped to accommodate components of the ventilator 250. Though the example housing 260 is generally cubic in shape to provide improved portability, other shapes can be used. The housing 260 includes openings (ports) for connecting to and/or accommodating (at least partially) externally disposed components such as but not limited to an oxygen inlet, compressed air inlet, air/oxygen mixing dial, PEEP valve, 3-way valve, pressure monitoring lines, system pressure setting regulator, analog system pressure reading (e.g., a dial and needle display), continuous PEEP flow pressure setting knob, state (mode select) switch, LED indicators, LCD operation switch (e.g., page button), LCD display, respiration rate knob, and inspiration time (I time) knob.

A power supply conduit 262 extends from the housing for powering the ventilator. A movable (e.g., pivotable and slidable) cover 264 can be provided for selectively covering exposed components. Feet 266 may be coupled to the housing for supporting the housing.

Referring now to FIG. 11, in some example embodiments, the controller 241 for the ventilator 250 is provided by (e.g., is embodied in, includes, or is incorporated in) a Printed Circuit Board Assembly (PCBA) 300 to enhance safety and functionality for the ventilator. The PCBA 300, which can be contained within the housing 260, also can allow for easier assembly of the ventilator, as all sensors can simply be plugged into their proper ports, as well as safer circuitry, as wires that have the risk of being disconnected can be omitted.

An example PCBA 300 is a four-layer, top assembly board with inner layers for ground and 5-volt (5V) signals. The PCBA 300 houses a microcontroller 301, one or more critical safety components, sensor connector ports, and other components for keeping operation of the ventilator reliable and safe. Example circuits can include one or more safety measures for reducing shortages or board failures, such as but not limited to ESD diodes, filter capacitors, decoupling capacitors, or distributed capacitance. These additions are possible at least in part because of the compact size of the example board and the multilayer construction. An example PCBA circuit can use readily available electrical components, and the PCB manufacturing process can be scaled.

In an example operation, the PCBA 300 the microcontroller 301 drives a solenoid power relay (e.g., a Single Pole Single Throw (SPST) relay) 302, which pulls a voltage (e.g., 24V) from a board power input port 303 to power a solenoid connected to solenoid connector 304 and ultimately control breaths. Connectors 310, 311 for connecting to the inspiration time potentiometer knob (I time) and to the respiration rate potentiometer are provided to control the breathing cycle.

In example ventilators, knobs are provided for the respiratory rate knob and inspiration time potentiometers to control (e.g., tune) the respiratory rate and the inspiratory time, respectively. In an example embodiment, to allow the user a wide range of inputs for both Inspiration Time and Respiration Rate, two 10 kΩ potentiometer knobs may be used, with 5 volts being used as the input. The input voltage is processed and used to control the actuation cycle of the solenoid.

A connector 312 for the state (mode) select switch (FIGS. 9-10) allows the user to select the ventilation mode. A connector 313 for the LCD switch controls the information being shown on indicators such as LCD displays (FIG. 9), which may be connected via LCD connection port 330. An example LCD utilizes an I2C bus to present user inputs as well as collecting vital data gathered from each ventilation cycle. Example LCDs can show ventilation cycle information (and other information, if desired) to the user, including but not limited to factors of a ventilation cycle such as respiratory rate, inspiratory time (e.g., as selected using the respiratory rate knob and inspiration time knob), I:E ratio, delivered (inspiratory) pressure, and inspiratory or expiratory flow. The LCD switch in an example embodiment can be used to toggle between critical information (e.g., on a first page) and secondary information (e.g., on a second page) on the ventilation cycle. The second screen may be configured to time out and return to the first.

Live graphical data may also be provided on the LCD display and/or on a connected computer or other processing device such as a mobile communication device (e.g., smartphone, tablet computer, etc.). Example indicators can alternatively or additionally be provided for, as non-limiting examples, a visual representation of a heartbeat, ventilation cycle, and/or solenoid to show that code is executing and actuating.

Sensor connectors 320 can be provided to connect to sensors for monitoring pressure, flow, and oxygen readings at select locations on the ventilator, as described above. These values can be recorded and interpreted by the microcontroller 301. A USB port and USB-to-serial converter can also be provided, e.g., for uploading firmware and reading data.

Connectors 340, 341 provided for connecting to Light Emitting Diodes (LEDs) (or other visible indicators) and to a buzzer can provide visual and audio indicators to the user, e.g., as an alarm indicator in the event of potentially dangerous system operating parameters. The buzzer can be used, for instance, to signal to an operator that an issue has arisen.

A missing pulse detector (MPD) 342 can be configured to ensure that the microcontroller 301 is functioning properly, e.g., by reading a constant pulse sent by the microcontroller 301 using methods that will be appreciated by those of ordinary skill in the art. If that pulse is missed, the missing pulse detector 342, e.g., an LM555 missing pulse detector can be configured to flip a system input relay 343, changing the driving signal of the system from the microcontroller 301 to a watchdog or back-up timer 344, e.g., an LM555 back-up timer utilizing three 5 kΩ resistors and two comparators. The back-up timer 344 can be configured to provide a pre-set ventilation cycle to continue delivering breaths if the microcontroller 301 becomes unresponsive.

In an example embodiment, the MPD receives a regular pulse from the microcontroller every 0.1 seconds, signifying that the microcontroller is properly working. If the microcontroller faults in any way, this pulse will no longer be sent to the MPD. The MPD 342 detects when there is more than 1.1 seconds between heartbeat pulses, which should occur every 0.1 seconds, and if so changes its output from a Boolean LOW (0 Volts) to HIGH (5 Volts). The back-up timer 344 will take over when MPD is triggered, triggering with an IT of 1 second, an I:E ratio of 1:2, and a RR of 20 bpm. Although this breathing cycle may not be ideal for all patients, it will be sufficient to allow them to continue to respirate for the short time it will take for the system to be rebooted or replaced by healthcare professionals.

As mentioned above, a significant concern for mechanical ventilators is dead space in the patient line, particularly but not exclusively with most low-cost emergency ventilation systems. Dead space is the volume of a breath that does not participate in gas exchange. Providing the continuous PEEP line as in the ventilators 50, 250 in example embodiments can reduce dead space.

Example continuous PEEP lines can provide other unique benefits. For instance, since the example PEEP line can provide a constant flow to the patient's lungs, convective forces cause the air and $CO_2$ to mix, decreasing the $CO_2$ concentration.

Figure 12:
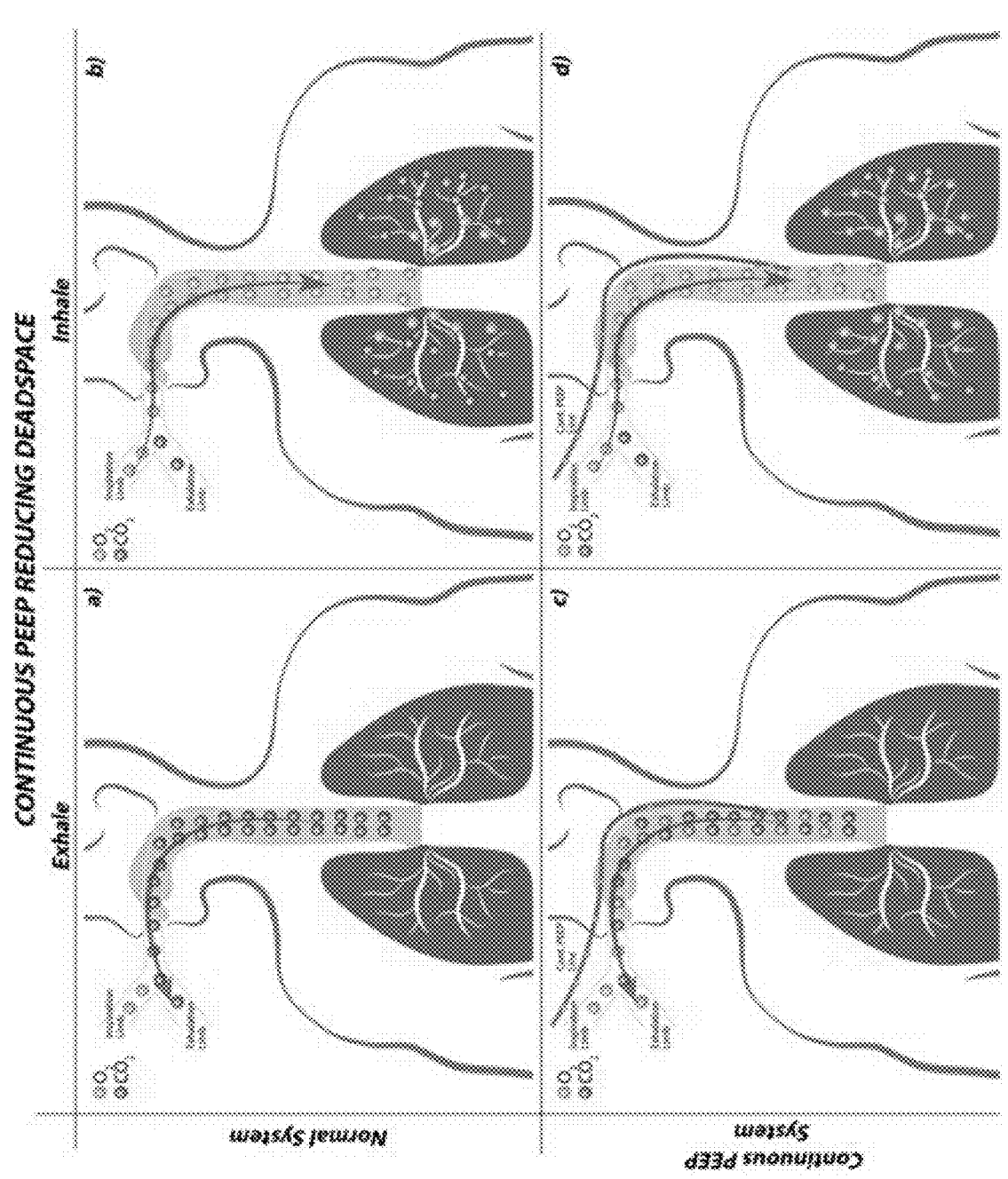
FIG. 12 illustrates how an example continuous PEEP limb reduces dead spaces in a patient's lungs as compared to a conventional ventilator system.

FIG. 12 illustrates how the example continuous PEEP limb reduces dead spaces in a patient's lungs as compared to a conventional ventilator system. The figure shows the example continuous PEEP limb joining the inspiration limb in an intubation tube placed within a patient. Particularly, FIG. 12 a) (top left) shows $CO_2$ build up during exhalation with a standard ventilation setup, and b) demonstrates how dead-space $CO_2$ affects the patient's lungs during inspiration. In contrast, FIG. 12 c) shows how a continuous PEEP line according to example embodiments that is placed inside an intubation tube (or as close to the lung as possible) can help remove $CO_2$ from a patient's airway, while FIG. 12 d) (bottom right) demonstrates how the reduced $CO_2$ build-up minimizes the amount of $CO_2$ pushed back into the lungs.

Figure 13:
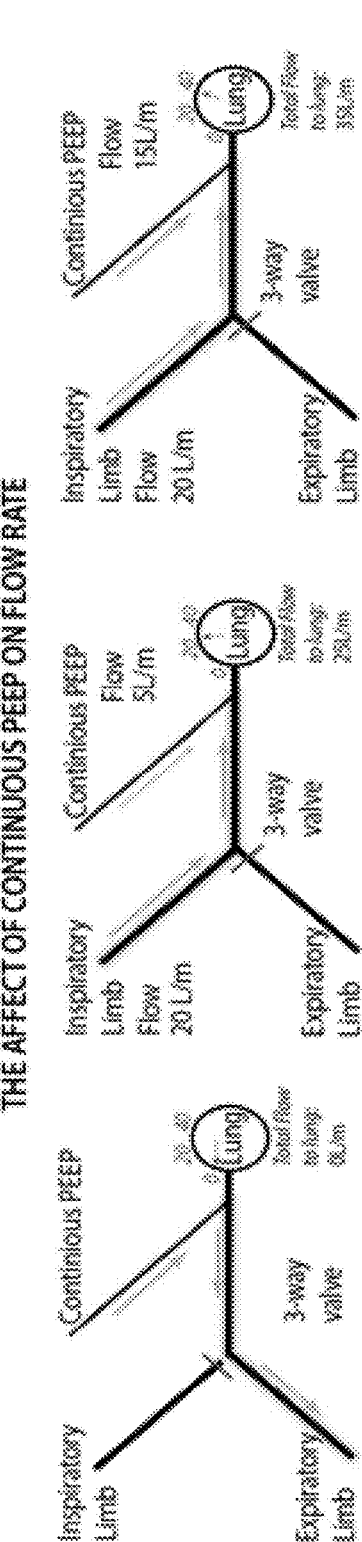
FIG. 13 illustrates how an example continuous PEEP limb can help increase the inspiration flow rate and, in turn, tidal volume (TV).

FIG. 13 illustrates how the example continuous PEEP limb can also help increase the inspiration flow rate and, in turn, tidal volume (TV). During exhalation, the flow helps push $CO_2$ out of the lungs, but due to the lower pressure at the expiration limb's outlet, no air is delivered to the lung. Upon inspiration, the exhalation limb is closed, and the example continuous PEEP, in addition to the inspiratory flow, is delivered to the patient's lung. This increase in TV is significant at least because it can enable lower CV (flow coefficient) components within the entire system, which reduces system cost.

Figure 14:
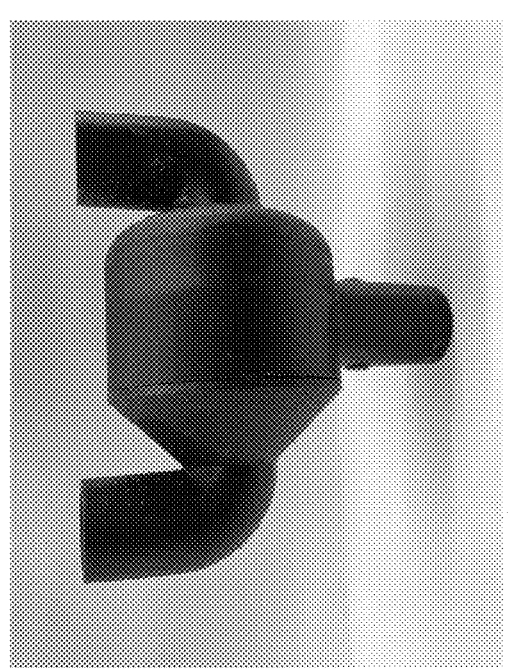
FIGS. 14-15 are perspective and elevation views (exploded in FIG. 15, left; assembled and partially cutaway in FIG. 15, right) of an example 3-way valve.
Figure 14:
Figure 15:
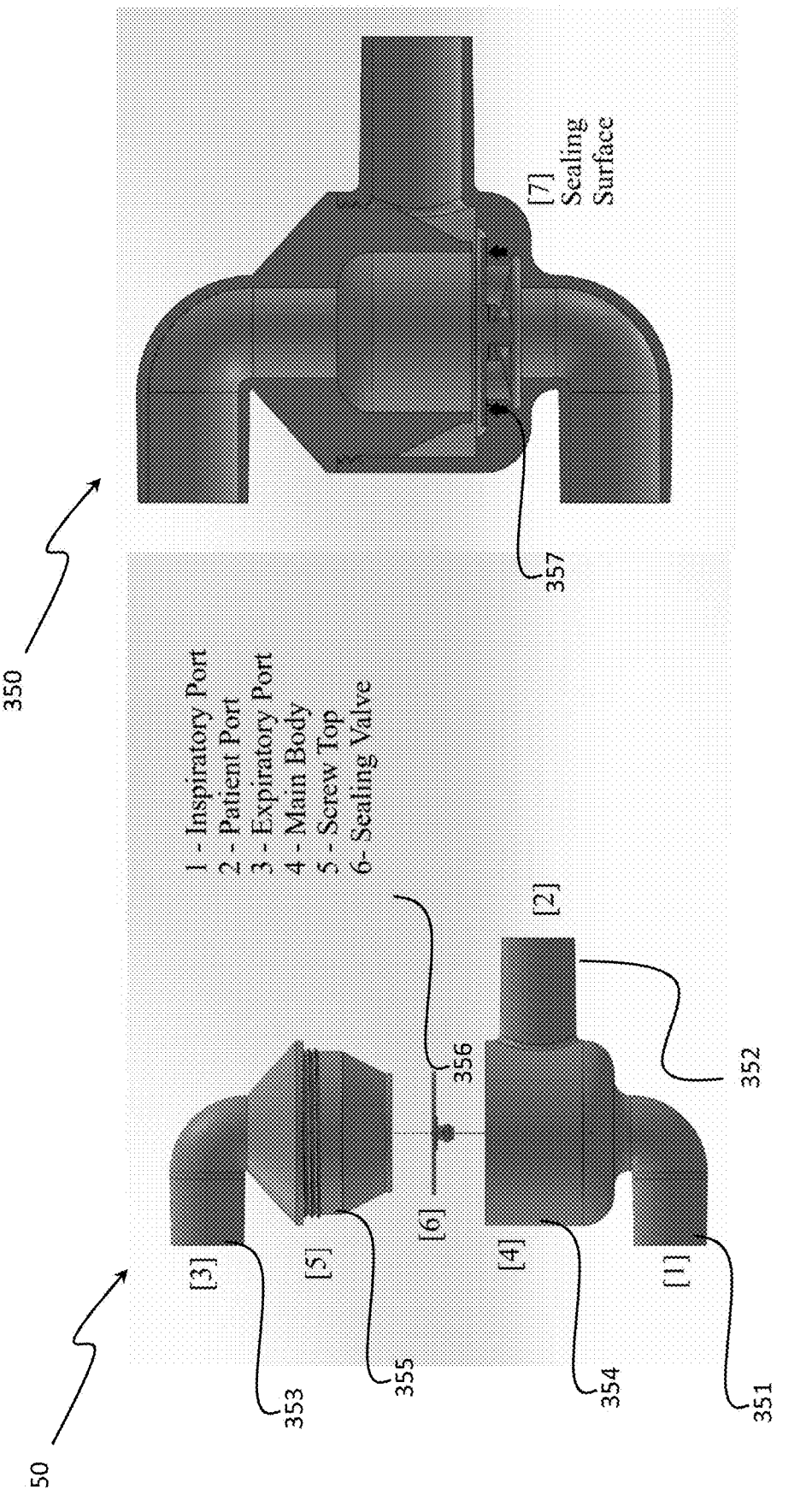

FIGS. 14-15 further illustrates features of an example 3-way valve 350, which can be used for one-way valves 148, 149. The example 3-way valve 350 is formed using additive manufacturing (e.g., 3D printing) with biocompatible materials. In currently used ventilators the path of inhalation (the clean, oxygen rich air coming into the patient) and that of exhalation (the air coming out of the patient) are conventionally controlled by two solenoids. These components are often expensive and require stringent coding to function properly. In contrast, the example three-way valve 350 can be used to further reduce cost and complexity for example ventilators herein.

The example three-way valve 350 includes a main body 354 containing an inlet (inspiratory or inhalation) port 351 and a patient port 352 and a connected (e.g., screwed-on or otherwise fastened) component 355 containing the exhale port 353. A valve such as an umbrella valve 356 is placed in the interior surface of the main body 354, and the component 355 is connected to the main body, e.g., screwed on.

The example three-way valve 350 is designed in such a manner that the bottom of the expiratory port 355 is positioned below the patient port 352. In a non-limiting example, the separation between sealing surface 357 and patient port 352 is 2 mm. This design ensures that the exhalation limb is closed during inspiration by sealing valve 356, while also ensuring that exhalation limb does not remain blocked during the patients expiratory phase by sealing valve 356.

Using suitable connections, for instance 22 mm internal diameter connections, the inspiratory port 351 can then be connected to the ventilation device, and the patient port 352 can be connected to the patient. The exhalation port 353 can be left open to the atmosphere or may be attached to a valve to regulate positive end expiratory pressure.

During inhalation, fluid flows through the inspiratory port 351, pushes the valve 406 up to seal the expiatory path at sealing surface 357, as shown in the right portion of FIG. 15, and proceeds to the patient through the patient port 352. During exhalation, the fluid from the patient comes in through the patient port 352, pushes the valve 356 down, and the fluid exits through the exhale port 353. In example embodiments, a relatively more porous sealing surface 357 and a relatively wider umbrella valve are provided to improve exhalation flow, decreasing the risk of auto PEEP-ing.

Figure 16:
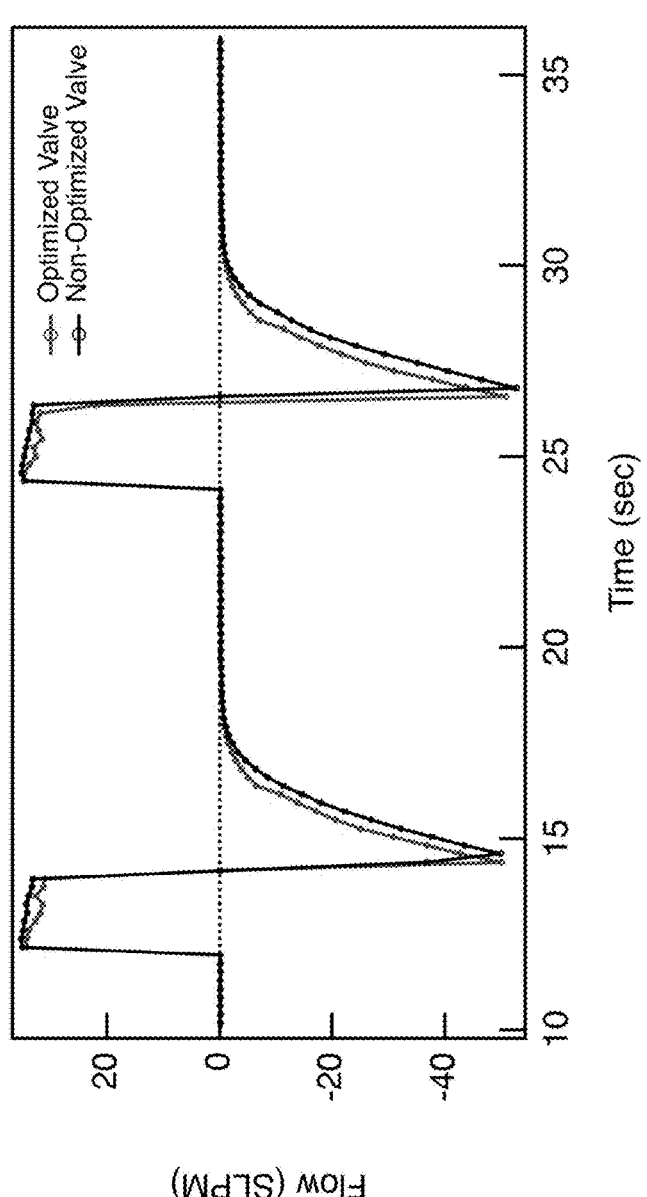
FIG. 16 shows valve response data for the example 3-way valve of FIGS. 14-15.

The valve response data shown in FIG. 16 illustrates that the example 3-way valve response is faster than a non-optimized valve and allows air to be expelled quickly from the lung. This is helpful, for instance, in preventing auto-PEEP under high respiratory rates (such as typical with low TV respiratory treatment).

Figure 17:
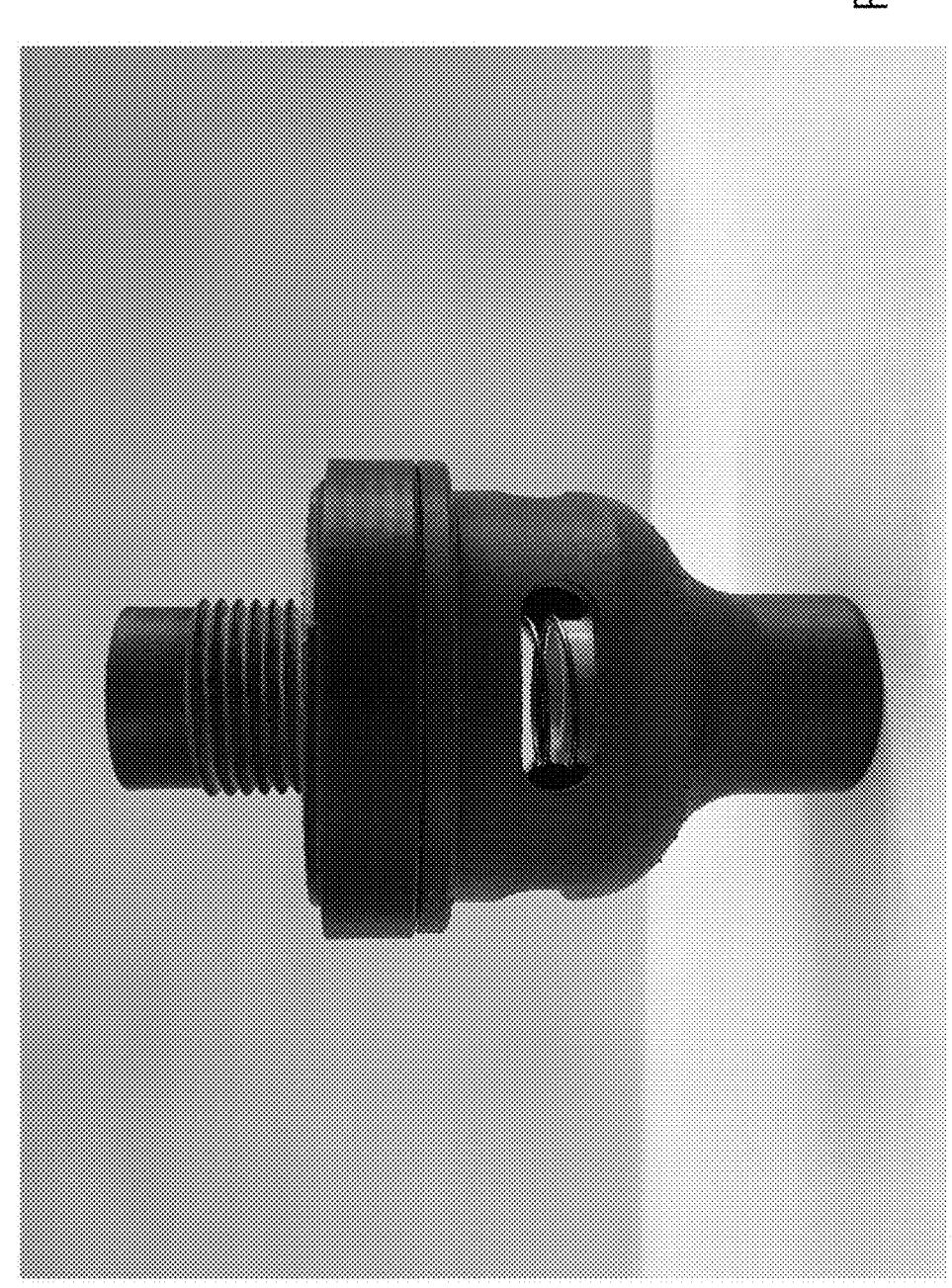
FIGS. 17-18 show features of an example PEEP valve.
Figure 18:
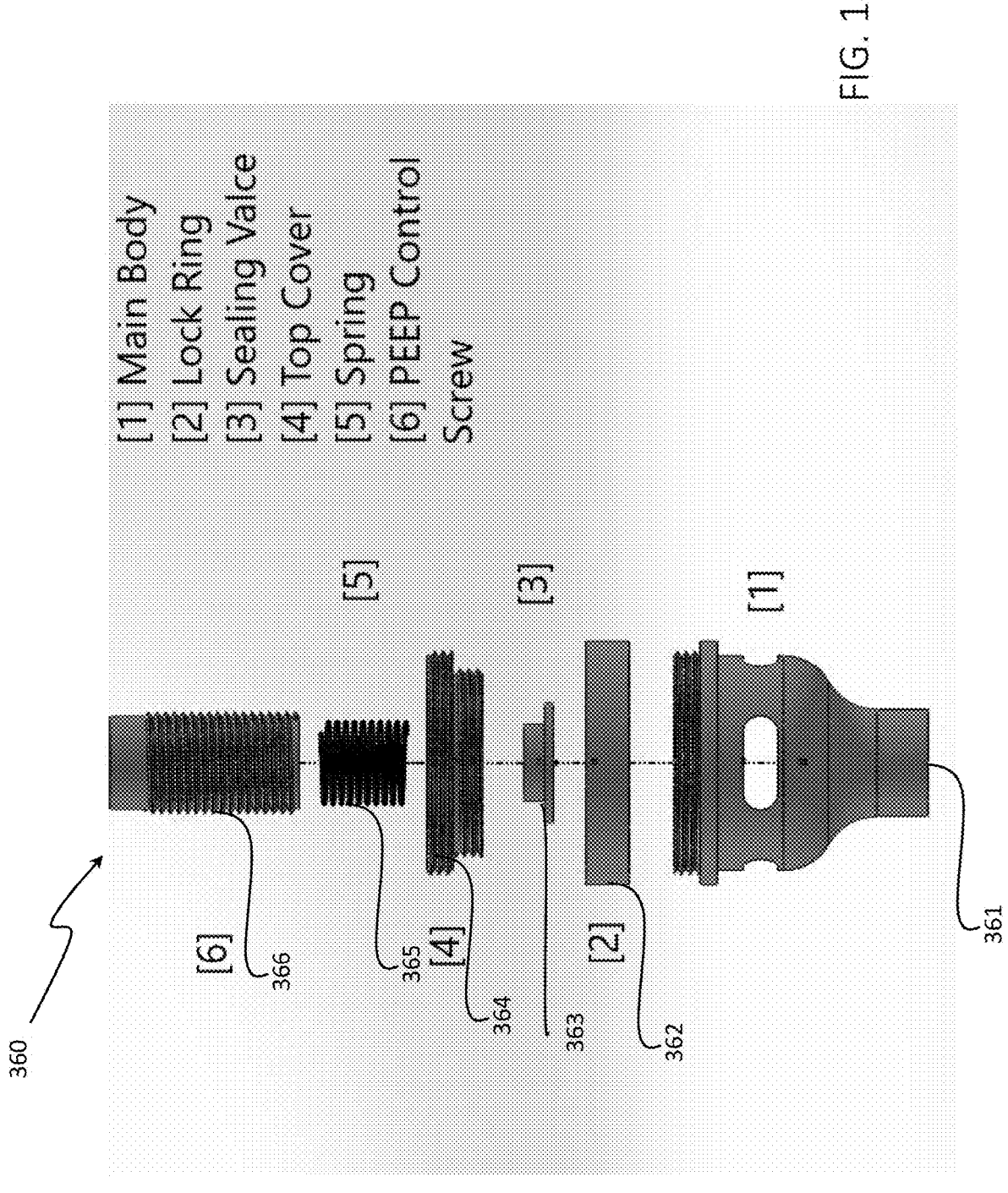

FIGS. 17-18 show features of an example PEEP valve 360, such as can be used for exhale PEEP regulator 166. Positive end-expiratory pressure (PEEP) is the pressure in the lungs that exists at the end of expiration and is used to prevent the lungs from collapsing during exhalation. Physicians commonly set PEEP between 5 and 20 cm $H_2O$. The example PEEP valve 360 allows PEEP to be set below, for instance, 10 cm $H_2O$, which is not possible for some conventional valves for certain settings.

The example PEEP valve 360, which in an example embodiment is 3D printed from biocompatible materials, includes a main body 361 having upper threads that engage inner threads of a locking ring 362. A top cover 364 is disposed within an opening of the locking ring 362. The example PEEP valve 360 further includes a spring 365 extending through a central portion of the top cover 364. The spring 365 regulates the pressure in a patient's lungs by limiting the amount of air that can be expelled during exhalation. A control mechanism such as a control screw 366 extends through the central portion of the top cover 364 surrounding the spring having outer threads that engage with inner threads of the top cover. The control screw 366 has an inner surface configured to selectively engage with a first end of the spring 365 to compress the spring. For instance, by rotating the control screw 366, the spring 365 is compressed, applying more force on a sealing valve 363 in contact with (e.g., mated with) a second end of the spring, and increasing pressure on the lung Mechanical valves can be provided in example ventilators for tuning the device to meet a patient's needs. For instance, the example PEEP flow pressure valve, e.g., throttle valve 112, can be configured to be tuned with a small circular dial. This dial can lock into place when pushed-in, which provides an additional safety feature that does not allow for the valve to turn if bumped.

The example mixing valve, e.g., valve 160, can be embodied in a 3-way ball valve that mixes the incoming oxygen and air inputs. The mixture can be changed by turning a valve lever in the 3-way ball valve. An example lever can be configured to let in only air, only oxygen, or a mixture of both at marked 20% (or other) concentration increments.

Figure 19:
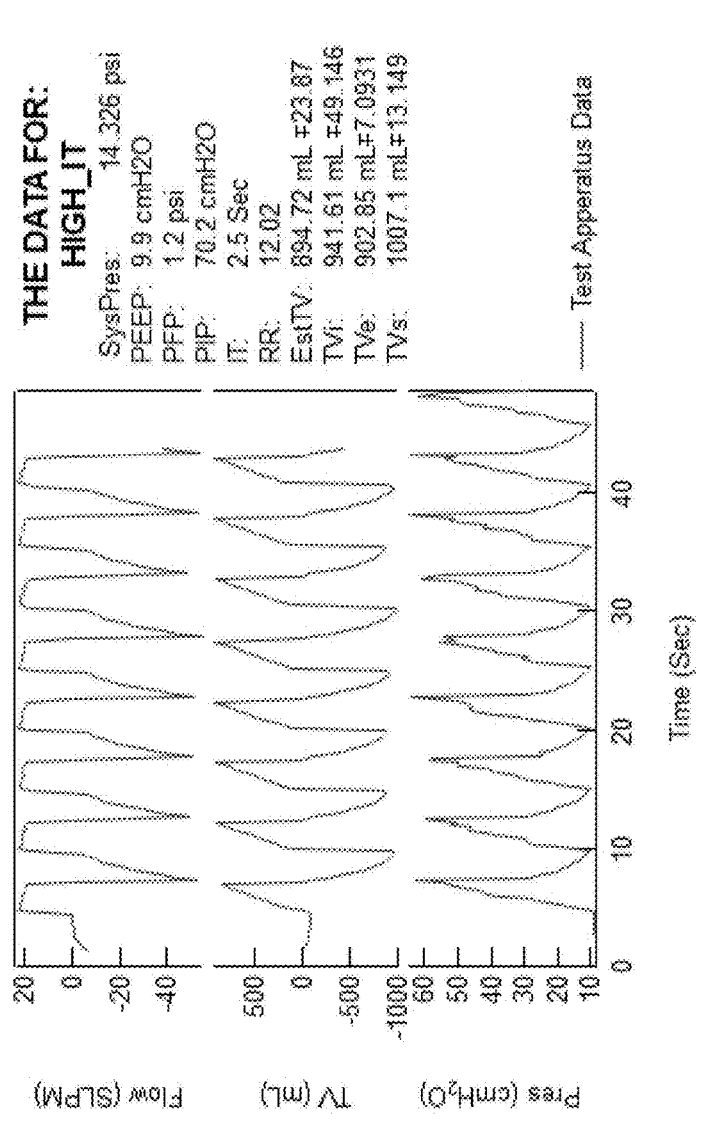
FIGS. 19-21 shows example patient metric plots for high I-time (IT) (FIG. 19), low PEEP (FIG. 20) and high respiratory rates (FIG. 21).
Figure 20:
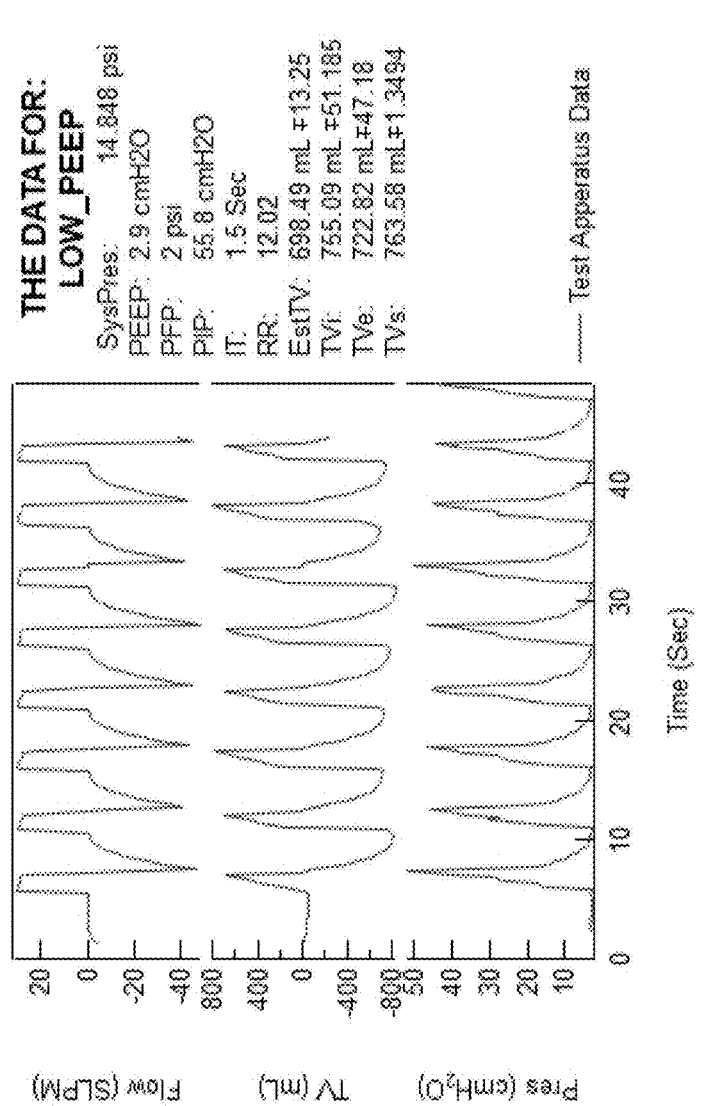
Figure 21:
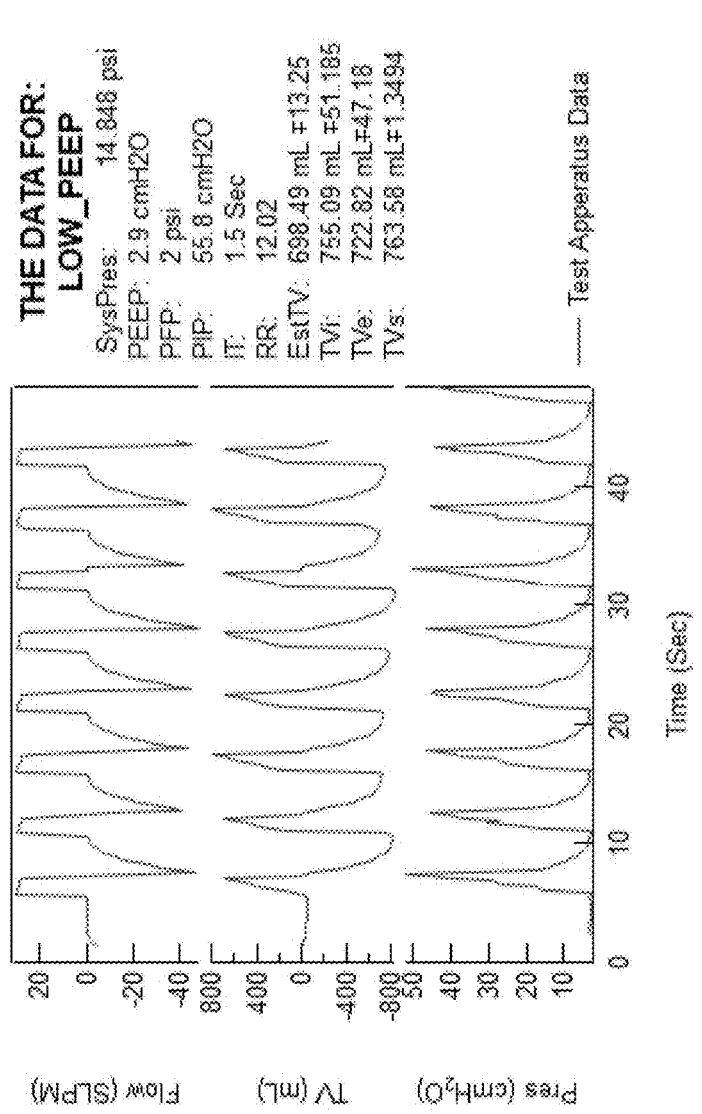
Figure 22:
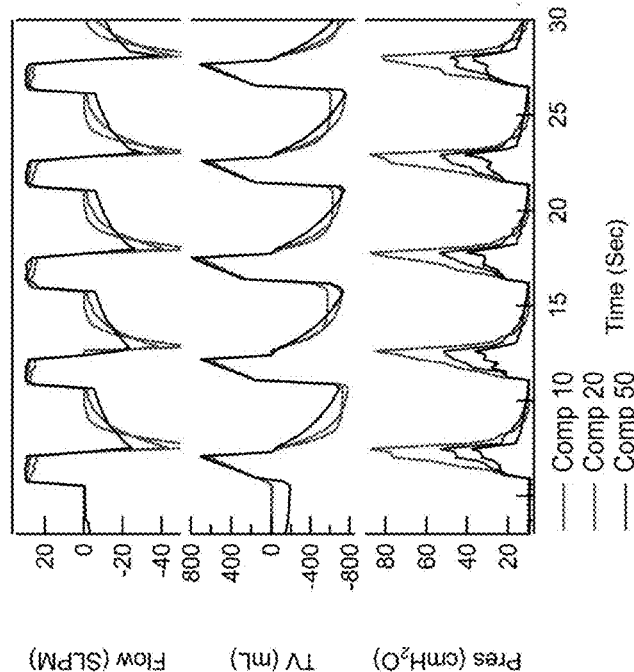
FIG. 22 shows example system performance with various lung compliances.
Figure 23:
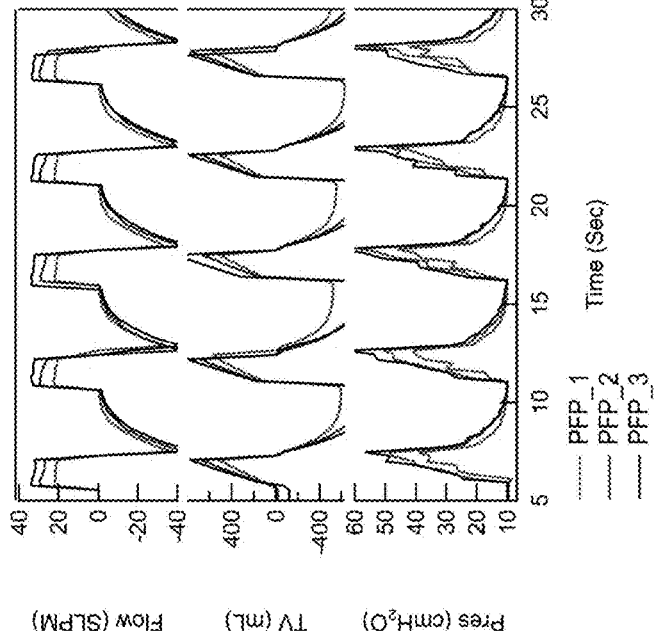
FIG. 23 shows example system performance with different PEEP flow pressures (PFP).
Figure 24:
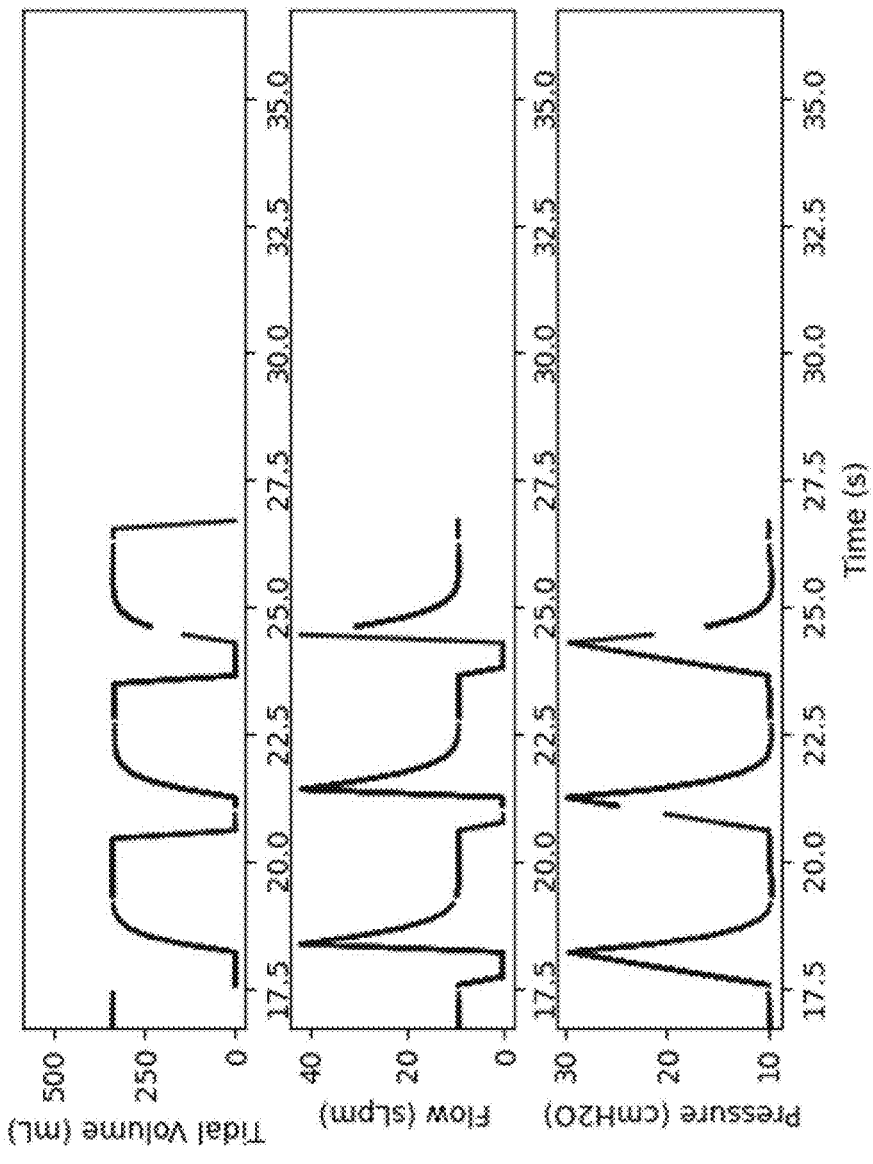
FIG. 24 shows a plot of real time Pressure, Flow, and Tidal Volume vs. Time.

Table 1 below displays a range of functionality of an example ventilator. FIGS. 19-21 shows example patient metric plots for high I-time (IT) (FIG. 19), low PEEP (FIG. 20) and high respiratory rates (FIG. 21). FIG. 22 shows example system performance with various lung compliances. FIG. 23 shows example system performance with different PEEP flow pressures (PFP). FIG. 24 shows a plot of real time Pressure, Flow, and Tidal Volume vs. Time.

TABLE 1

| Tidal Volume (mL) | Inspiratory Time (Sec) | PEEP (cmH2O) | Respiratory Rate (BPM) | Max PIP (cmH2O) |
|---|---|---|---|---|
| 200-1100 | .1-3.0 | 5-20 | 5-60 | 40-90 |

Figure 25:
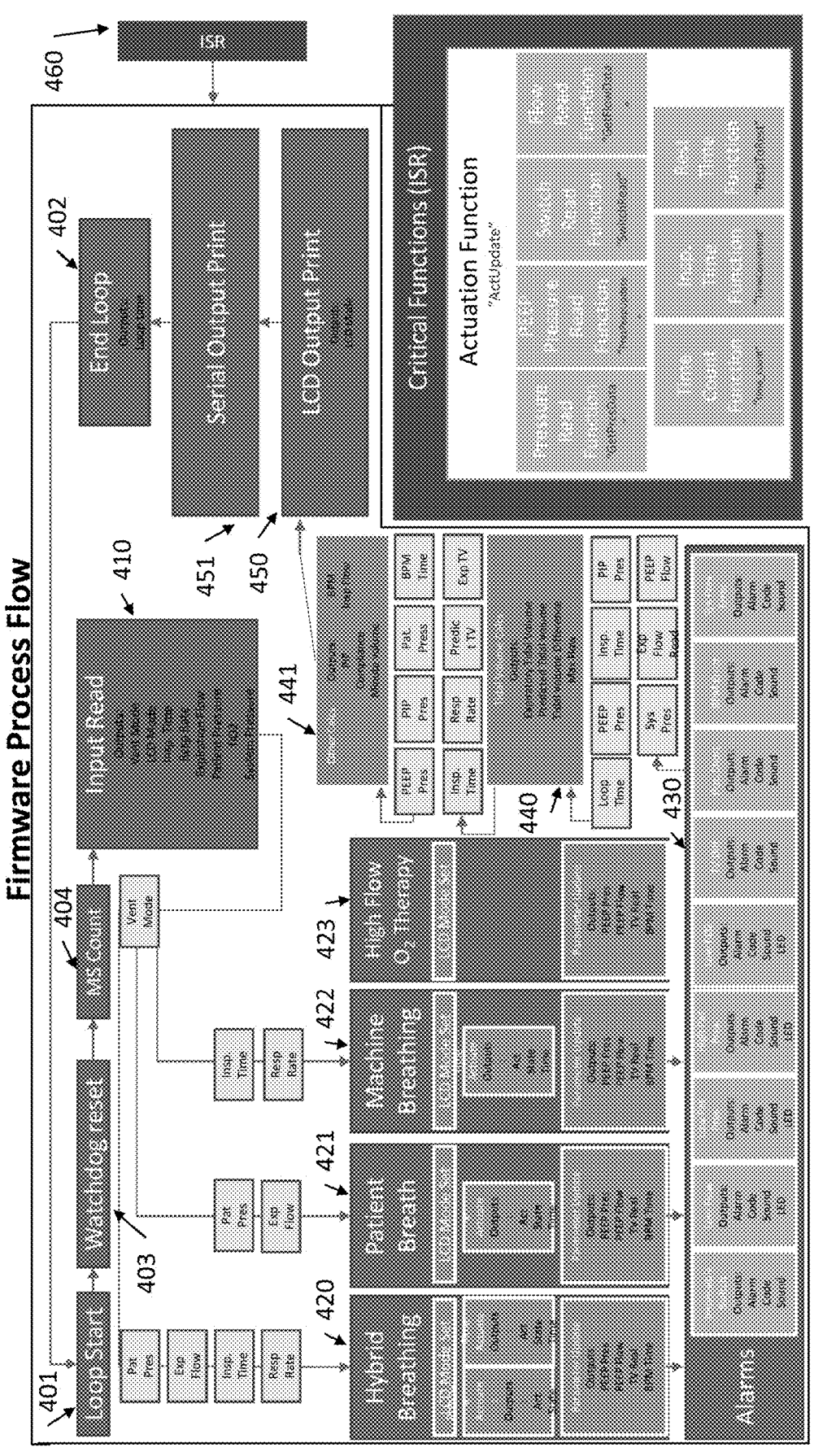
FIG. 25 shows components (e.g., functional blocks) in an example process flow, which may be implemented by firmware or software code executable by the controller of an example ventilator.

FIG. 25 shows components (blocks) in an example process flow 400, which may be implemented by firmware or software code executable by the controller 241. The example ventilator control code for the process flow 400 is contained within a loop that repeatedly cycles from a Loop Start block 401 to an End Loop block 402, calling various functions within. A Watchdog Timer block is used to reboot the microcontroller 241 if a Watchdog Reset block 403 is not triggered at least every 2 seconds (or other interval). A millisecond counter, shown as MS Count 404, is iterated every 10 ms (or other interval) to keep accurate time within the loop and is used in several functions throughout. MS count 404 is related to time count which is iterated within ISR 460.

The example code gathers several inputs during an Input Read block 410, such as Ventilation Mode, LCD Mode, Inspiratory Time, Respiratory Rate, Expiration Flow, Patient Pressure, Oxygen flow (fiO2), and System Pressure. These inputs can be used to control all aspects of the ventilation cycle and deliver critical information to the user.

Ventilation Modes

Based on the ventilation mode selected during the Input Read block 410, one of four possible ventilation modes are used when providing ventilation. Hybrid Breathing block

420 will use the patient pressure sensor and the MS Count 404 timer to deliver a breath when the patient attempts to inhale or deliver a breath on a timed cycle. Patient Breathing block 421 will use the patient pressure sensor to deliver a breath only when the patient attempts to inhale. If no breath is sensed within a specified time window, an emergency breath is delivered. Machine Breathing block 422 will use the MS Count 404 timer to deliver a breath on a timed cycle. An alternative or additional mode, High Flow Oxygen Therapy 423 can be provided in an additional block (not shown) to deliver a constant flow of oxygenated air, without any timed breaths.

Alarms

A variety of alarm blocks 430 can be provided to alert the user to any issues that may arise during the ventilation cycle. Examples include, but are not limited to: Impossible Switch, Low Flow, Low Patient Pressure, High Patient Pressure, Low fiO2, TV Differential, Potentiometer Knob Short Circuit, BPM Error, or System Pressure Error. These alarms can be triggered if a value is above or below its respective preset maximum or minimum value. Each alarm can be associated with an audio alarm and alarm code displayed on the LCD, while the most critical can have a visual alarm indicator as well.

System Calculations

The values gathered during Input Read block 410 can be utilized to calculate important system values that cannot be measured. This includes, for instance, tidal volume (TV) and flow calculations (block 440) as well as a variety of other calculations, such as PIP, Compliance, Minute Volume, BPM, and Inspiratory Flow (block 441) that may be useful for successful ventilation.

Outputs

The example system can output the pertinent ventilation information to an LCD screen during operation of an LCD Output Print block 450. This is useful for the operator to be able to read the necessary information and adjust the system accordingly. The example system can also output this information to the serial port of a connected computer during a Serial Output Print block 451. This is done so that the ventilation cycle data can be gathered and analyzed.

Critical Interrupt

An interrupt block 460 can be provided to ensure that the example system critical functions are executed properly and on their determined time interval. The functions that are deemed system critical are those that are necessary to the actuation of the ventilator and to keeping the patient breathing properly. By using an interrupt, these functions can be executed regardless of the MS Count 404 timer and will be executed if the system happens to be stuck in a non-critical function.

Watchdog Timer and Safety Considerations

To provide safer system operation for the user and patient, and meet regulator requirements (e.g., the safety requirements of the FDA), the example software/firmware can include several safety measures. One example safety measure is a watchdog timer, as described above. An example watchdog timer is a timer that is connected to the "Reset" line of the microcontroller 241. If the watchdog timer is not reset periodically within the code, the watchdog timer will pull the "Reset" line and reset the microcontroller completely. This safety feature allows the software to be constantly monitored and reset in the event of a crash, without needing any user interaction.

Another example safety measure is that all ventilator functions deemed "safety critical" may be executed within an interrupt. An interrupt is a portion of code that will execute after a set amount of time, such as but not limited to 10 milliseconds, regardless of the current position within the loop. After the interrupt has executed its functions, the code will pick up where it left off within the loop. Safety critical functions are those that are essential to patient safety while ventilating and may include, but are not limited to, solenoid actuation, pressure and flow sensor reading, ventilation mode reading, and inspiration time and respiration rate input. Including the critical functions within the interrupt ensures that the critical functions will execute on time and not be skipped within the complex functions of the code as a whole.

Yet another safety measure within the code is detecting possible short circuits within various electronic components, such as the potentiometer knobs and switches. This detection can be done by analyzing the inputs of the knobs and switches and triggering an error if the reading is an unknown state or too high or too low of voltage. In doing so, the example system can notify the healthcare worker if they have input incorrect parameters.

Alarms and Safety Features

As explained above, the ventilator can be equipped with a multitude of alarms that are critical to ensure safe operation of the device. Example alarms include, but are not limited to: low flow (e.g., from Insp/Exp line disconnection, valve failure, regulator failure, solenoid failure, poor mask fit); low inspiratory pressure (e.g., from valve failure, regulator failure, PEEP valve failure, poor mask fit), or high inspiratory pressure (e.g., from Insp/Exp line kink, valve failure, regulator failure, solenoid failure, airway blockage); low FiO2 (e.g., from Mixing chamber failure, $CO_2$ buildup), tidal volume difference/error, electrical shortages (e.g., from a switch failure), low or high breath per minute count (e.g., from solenoid failure), and low or high system operating pressure (e.g., from Air/$O_2$ inlet disconnection or overpressurization). These alarms, or a combination of multiple alarms, will alert the healthcare professional to potentially dangerous operating conditions or system failure. The user has the ability to set the alarm trigger threshold within the software, giving full customization of the ventilation cycle.

In addition to the various alarms within the system, the ventilator can also contain one or more safety measures that will automatically combat system failure. One safety feature is the missing pulse detector MPD and back up timer described above.

Another example safety measure is a blow-off valve. The blow-off valve is a part of the breathing circuit that ensures the patient does not experience dangerously high inspiration pressures. This valve can be connected to the breathing circuit, as close to the patient's mouth as possible, and opens at a set pressure. If the patient's airway becomes blocked or the ventilator is actuating too often, this valve allows the pressure to be released to the atmosphere instead of overpressurizing and perhaps harming the patient's lungs.

Yet another safety feature is the three-way valve that can be attached to the line between the solenoid and the breathing circuit. This valve allows atmospheric air to flow into the breathing circuit but does not allow the air delivered by the solenoid to escape. This valve allows the patient to take a breath, even if the ventilator is in CMV mode with the solenoid closed. Although the provided air on this emergency breath will be atmospheric air and not the oxygenated air being provided through the ventilator, it is an essential part of the ventilator that prevents the patient from being denied a breath.

In an example use of the ventilator a test lung was paired with a software program that measured a set of parameters in real-time, which include breath rate, inspiratory/expiratory time, tidal volume, flow rate, pressure, compliance, and resistance. It is useful for the tidal volume to be displayed and easily tuned. Often, the respiratory therapist or ventilator technician will adjust the tidal volume based on the patient response and their condition. In order to display an accurate tidal volume, two avenues were employed known as the "tidal volume real" and the "tidal volume predicted." The code uses the peak inspiratory pressure (PIP), PEEP, and time, to calculate the "tidal volume real" and display it on the LCD screen. The "tidal volume predicted" uses an algorithm created from test data to calculate tidal volume based on the ventilation cycle parameters.

Extensive testing and data acquisition were performed. The mock lung allowed for testing different patient conditions. The pulmonary resistance (Rp) can be increased to mimic patients that have conditions like asthma. The Rp can be set to 5, 20, or 50 (cm/L/s). Lung compliance is the lung's ability to stretch and expand which affects inhalation as well as exhalation. The compliance (C) of the lung can be set by adding springs to the lung based on how sick the patient is and can be calculated based on the volume/pressure ratio of the lung. The compliance can be set to 10, 20, or no springs which is assumed to be 50 (mL/cm). Once the data was collected, it was analyzed in software (Igor) to create an example algorithm for tidal volume prediction.

Regression Analysis

Igor is a powerful data analysis software package that was used to determine the relationships between ventilator settings and patient behavior. an example predictive model based on these relationships can be utilized in example embodiments to reduce the number of onboard sensors (reducing system cost) and also alert doctors to patient behavior that would indicate deteriorating patient health or an external breathing circuit leak.

Figure 26:
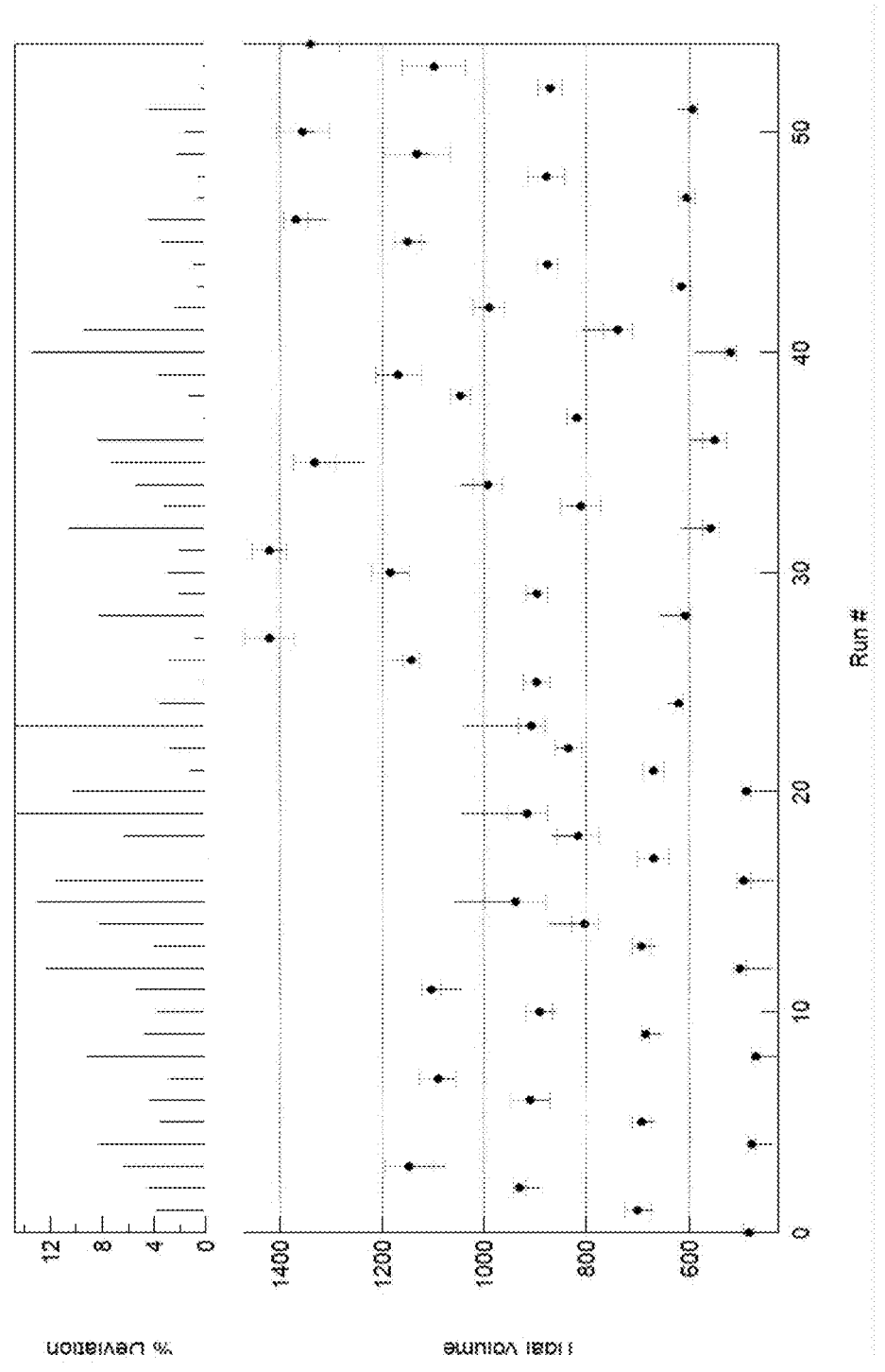
FIG. 26 illustrates example input data that may be used to generate a predictive algorithm via regression analysis in an example operation.

Data collected during test runs could be immediately plotted and used to optimize the settings-behavior algorithm. FIG. 26 shows some of the data used to generate the predictive algorithm via regression analysis. In FIG. 26, black circles are individual data points collected during testing. The top of the blue (light horizontal) lines coming from the black circles represent a predicted TV that is greater than the actual TV. Conversely red lines represent a predicted TV that is less than the actual measured TV. The percent error of each TV predict data point is shown on the top quarter of the graph. TV may be calculated using the following example equation:

$$TV=a*IT+b*PFP+|c|+SysPres+d*PEEP+e$$
$$\sqrt{PIP}+f*Resistance+g*IT^2+h*PFP^2+i*IT*PFP$$

These values can be controlled by the solenoid and can be triggered by pressure sensor 151, 161 when the patient needs a breath or at regularly scheduled intervals as determined for each patient. The oxygen and air ratio can be controlled by changing the oxygen flow rate at the oxygen source 102. This can be tailored for each patient.

Various features and aspects of ventilators 50, 250 have been shown and described. In example operation, when a patient is not breathing, the example PEEP flow can constantly remove $CO_2$. The patient's breath can then close off an example valve, such as the 3-way valves shown and described herein. Two flows, inspiratory and continuous PEEP, can go the patient's lungs.

The continuous PEEP flow provided by the example PEEP flow limb (line), is believed to be novel, and has not been possible with conventional ventilators. Dead space is minimized or omitted, as the example continuous PEEP line can engage or be delivered directly to a patient's mouth, or to an intubation tube where inlet is down in the patient's lungs.

The number of sensors used for operation can be reduced compared to conventional ventilators. Example operational methods using example algorithms can allow for the use of inexpensive sensors, and relatively more expensive components can be avoided. The continuous PPEP flow avoids the need for high flow from the inspiratory limb, further reducing manufacturing and/or operation cost. Example features can work together in predictable ways, and example operations can be improved or enhanced with additional use and/or via machine learning (e.g., to improve example models).

All publications, patents, patent applications cited herein are hereby expressly incorporated by reference in their entireties for all purposes.

The foregoing description is merely illustrative in nature and is in no way intended to limit the disclosure, its application, or uses. The broad teachings of the disclosure may be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure may be implemented in and/or combined with features of any of the other embodiments, even if that combination is not explicitly described. In other words, the described embodiments are not mutually exclusive, and permutations of one or more embodiments with one another remain within the scope of this disclosure.

Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. Also, in the foregoing description, numerous details are set forth to further describe and explain one or more embodiments. These details include system configurations, block module diagrams, flowcharts (including transaction diagrams), and accompanying written description. While these details are helpful to explain one or more embodiments of the disclosure, those skilled in the art will understand that these specific details are not required in order to practice the embodiments.

As will be appreciated by one skilled in the art, aspects of the present disclosure may be embodied as an apparatus that incorporates some software components. Accordingly, some embodiments of the present disclosure, or portions thereof, may combine one or more hardware components such as microprocessors, microcontrollers, or digital sequential logic, etc., such as a processor, or processors, with one or more software components (e.g., program code, firmware, resident software, micro-code, etc.) stored in a tangible computer-readable memory device such as a tangible computer memory device, that in combination form a specifically configured apparatus that performs the functions as described herein. These combinations that form specially-programmed devices may be generally referred to herein as modules. The software component portions of the modules may be written in any computer language and may be a portion of a monolithic code base, or may be developed in more discrete code portions such as is typical in object-oriented computer languages. In addition, the modules may be distributed across a plurality of computer platforms, servers, terminals, mobile devices and the like. A given module may even be implemented such that the described functions are performed by separate processors and/or computing hardware platforms.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

Those of ordinary skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of ordinary skill in the art would further appreciate that the various illustrative logical blocks, modules, circuits, and process steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in various ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or process described in connection with the embodiments discloses herein may be embodied directly in hardware, in a software module executed by a processor, or in a combination of the two. A software module may reside in RAM memory, flash memory, ROM memory, EPROM memory, EEPROM memory, registers, hard disk, solid state disk, optical media (e.g., CD-ROM), or any other form of transitory or non-transitory storage medium known in the art. An exemplary storage medium can be coupled to the processor such that the processor can read information from, and write information to, the storage medium. In the alternative, the storage medium can be integral to the processor. The processor and the storage medium may reside in an ASIC. The ASIC may reside in a user terminal. In the alternative, the processor and the storage medium may reside as discrete components in a user terminal.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A mechanical ventilator, comprising:
a fluid flow controller disposed to receive a mixed gas along at least a first line, the mixed gas including oxygen from an oxygen source and compressed air from a compressed air source/generator operably connected to the fluid flow controller, the fluid flow controller having a fluid flow controller output line operably connected to a patient line, the fluid flow controller being driven by an on-off valve to deliver the mixed gas to the patient line at appropriate intervals where a tidal volume (TV), inspiratory time, and/or peak inspiratory pressure (PIP) arise from fluid forced to a patient as dictated by the fluid flow controller;
a controller for the on-off valve;
a second line disposed to receive the mixed gas, the second line being configured to create a continuous, constantly flowing positive end-expiratory pressure (PEEP) for delivering the mixed gas along a PEEP output line to the patient line;
a junction combining the fluid flow controller output line and the PEEP output line, the patient line being operatively connected to and downstream of the junction; and
a uni-directional valve disposed within or upstream of the patient line and downstream of the fluid flow controller output line.

2. The mechanical ventilator of claim 1, wherein the fluid flow controller comprises a bag-valve-mask (BVM), the on/off valve, and a pneumatic actuator;
wherein the first line is operably connected to the BVM and is provided by a first compressed fluid output line for connecting to the compressed air source;
wherein a first oxygen output line for connecting to the oxygen source is operably connected to the BVM; and
wherein the on/off valve is disposed within the first compressed fluid output line.

3. The mechanical ventilator of claim 1, wherein the second line is operatively connected to a second compressed fluid output line and to a second oxygen output line;

wherein the mechanical ventilator further comprises a pressure control valve and a manometer disposed within each of the second compressed fluid output line and the second oxygen output line for controlling PEEP flow of the mixed gas along the PEEP output line.

4. The mechanical ventilator of claim 1, wherein the on/off valve is configured to control one or more of inspiration time or breath rate to the patient line; and
wherein the on/off valve is further configured to create a rhythmic flow of the mixed gas to the patient line.

5. The mechanical ventilator of claim 1, wherein the on/off valve is triggered by a pressure sensor disposed in the patient line.

6. The mechanical ventilator of claim 1, further comprising:
a pressure-release valve disposed within the patient line.

7. The mechanical ventilator of claim 1, wherein the controller is configured to control the ventilator to deliver a selected tidal volume (TV) at one or more inspiratory rates.

8. The mechanical ventilator of claim 1, wherein the controller is incorporated within a Printed Circuit Board Assembly (PCBA); and
wherein the fluid flow controller and the controller are contained within a housing.

9. The mechanical ventilator of claim 8,
wherein the ventilator further comprises an expiratory line disposed downstream of the uni-directional valve and having an output leading to environment;
wherein the uni-directional valve comprises a three-way check valve that is operably connected to the fluid flow controller output line, the patient line, and the expiratory line; and
wherein the housing includes ports for operatively connecting to the compressed air source, the oxygen source, and the three-way valve.

10. The mechanical ventilator of claim 1, further comprising:
a pressure sensor disposed along one or more of the patient line, the first line, and the second line, the pressure sensor(s) being coupled to the controller; and
an audible and/or visible alarm coupled to the controller for indicating an alarm condition based on values from the pressure sensor(s).

11. The mechanical ventilator of claim 1, further comprising:
a display coupled to the controller for indicating a status of the mechanical ventilator.

12. A method for operating a mechanical ventilator, the mechanical ventilator including a fluid flow controller disposed to receive a mixed gas along at least a first line, the mixed gas including oxygen from an oxygen source and compressed air from a compressed air source operably connected to the fluid flow controller, the fluid flow controller having a fluid flow controller output line operably connected to a patient line, the fluid flow controller being controlled by a pneumatic actuator powered by an on/off valve to deliver the mixed gas to the patient line at a tidal volume (TV), inspiratory time, and/or peak inspiratory pressure (PIP) provided by the fluid flow controller, a controller for controlling the on/off valve, a second line disposed to receive the mixed gas, the second line being configured to create a continuous positive end-expiratory pressure (PEEP) for delivering the mixed gas along a PEEP output line to the patient line, a junction combining the fluid flow controller output line and the PEEP output line, the patient line being operatively connected to and downstream of the junction, and a three-way valve disposed within or upstream of the patient line and downstream of the fluid flow controller output line, the method comprising:

receiving an inspiratory time, a patient pressure, and a respiratory rate;

providing a model that relates the inspiratory time, the patient pressure, a system pressure, and a patient flow pressure to a tidal volume;

determining one or more ventilator parameters to achieve delivery of desired breaths to a patient along the patient line using the model; and controlling operation of the mechanical ventilator based on the determined ventilator parameters.

13. The method of claim 12, wherein the model is trained using a machine learning algorithm.

14. The method of claim 12, wherein controlling operation occurs according to one or more of a plurality of selectable modes;

wherein the selectable modes comprises one or more of:

Continuous Machine Ventilation (CMV);

Intermediate Machine Ventilation (IMV);

Spontaneous Continuous Respiration (SCR); or

High Flow Oxygen Therapy (HFOT).

* * * * *